United States Patent
Horn et al.

(10) Patent No.: US 11,779,427 B2
(45) Date of Patent: Oct. 10, 2023

(54) MULTIPLE-INPUT-COUPLED ILLUMINATED MULTI-SPOT LASER PROBE

(71) Applicant: Alcon Inc., Fribourg (CH)

(72) Inventors: Jochen Horn, Pleasanton, CA (US); Alireza Mirsepassi, Irvine, CA (US); Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 592 days.

(21) Appl. No.: 16/217,346

(22) Filed: Dec. 12, 2018

(65) Prior Publication Data

US 2019/0175300 A1 Jun. 13, 2019

Related U.S. Application Data

(60) Provisional application No. 62/598,653, filed on Dec. 14, 2017, provisional application No. 62/597,550, filed on Dec. 12, 2017.

(51) Int. Cl.
| | | |
|---|---|---|
| *A61B 90/30* | (2016.01) | |
| *G02B 27/42* | (2006.01) | |
| *G02B 27/14* | (2006.01) | |
| *G02B 3/00* | (2006.01) | |
| *A61F 9/008* | (2006.01) | |
| *A61B 18/24* | (2006.01) | |
| *A61B 18/20* | (2006.01) | |
| *A61B 18/22* | (2006.01) | |

(Continued)

(52) U.S. Cl.
CPC .............. *A61B 90/30* (2016.02); *A61B 18/20* (2013.01); *A61B 18/24* (2013.01); *A61F 9/00821* (2013.01); *A61F 9/00823* (2013.01); *G02B 3/0087* (2013.01); *G02B 27/14* (2013.01); *G02B 27/425* (2013.01); *A61B 2018/2211* (2013.01); *A61B 2018/2244* (2013.01); *A61B 2018/2261* (2013.01); *A61B 2090/306* (2016.02); *A61F 2009/00863* (2013.01); *A61N 5/067* (2021.08); *A61N 2005/0663* (2013.01)

(58) Field of Classification Search
CPC .... A61B 90/30; A61B 18/20; A61B 2090/306
See application file for complete search history.

(56) References Cited

U.S. PATENT DOCUMENTS

| | | |
|---|---|---|
| 5,199,431 A | 4/1993 | Kittrell |
| 5,496,305 A | 3/1996 | Kittrell |

(Continued)

FOREIGN PATENT DOCUMENTS

| | | |
|---|---|---|
| JP | S5567702 U | 5/1980 |
| JP | A1994014936 A | 1/1994 |

(Continued)

OTHER PUBLICATIONS

Notice of Reasons of Rejection for Japanese Patent Application No. 2020-531771, dated Jan. 17, 2023, 12 pages.

*Primary Examiner* — James M Kish
*Assistant Examiner* — Jessica L Mullins
(74) *Attorney, Agent, or Firm* — PATTERSON + SHERIDAN, LLP

(57) ABSTRACT

Systems and methods for creating multi-spot laser light beams, multiplexing an illumination light and the multi-spot laser light beams, and delivering the multiplexed light to a surgical handpiece via a multi-core optical fiber cable.

10 Claims, 15 Drawing Sheets

(51) Int. Cl.
*A61N 5/06* (2006.01)
*A61N 5/067* (2006.01)

(56) References Cited

U.S. PATENT DOCUMENTS

| | | | |
|---|---|---|---|
| 5,625,638 A | 4/1997 | Trost | |
| 5,693,043 A | 12/1997 | Kittrell | |
| 5,921,981 A | 7/1999 | Bahmanyar et al. | |
| 6,066,128 A | 5/2000 | Bahmanyar et al. | |
| 6,096,028 A | 8/2000 | Bahmanyar et al. | |
| 6,893,432 B2 | 5/2005 | Intintoli et al. | |
| 7,189,226 B2 | 3/2007 | Auld et al. | |
| 7,302,142 B2 | 11/2007 | Conde | |
| 7,448,995 B2 | 11/2008 | Wiklof | |
| 7,566,173 B2 | 7/2009 | Auld et al. | |
| 8,398,240 B2 | 3/2013 | Smith | |
| 8,488,930 B2 | 7/2013 | Papac | |
| 8,498,506 B2 | 7/2013 | Smith | |
| 8,561,280 B2 | 10/2013 | Diao et al. | |
| 8,571,364 B2 | 10/2013 | Smith et al. | |
| 8,764,261 B2 | 7/2014 | Smith | |
| 8,903,475 B2 | 12/2014 | Brennan et al. | |
| 8,939,964 B2 | 1/2015 | Smith | |
| 8,951,244 B2 | 2/2015 | Smith | |
| 8,968,347 B2 | 3/2015 | McCollam | |
| 9,055,885 B2 | 6/2015 | Horvath | |
| 9,107,730 B2 | 8/2015 | Huculak et al. | |
| 9,211,214 B2 | 12/2015 | Rubinchik | |
| 9,308,128 B2 | 4/2016 | Smith | |
| 9,364,982 B2 | 6/2016 | Schaller | |
| 9,387,040 B2 | 7/2016 | Smith | |
| 9,402,643 B2 | 8/2016 | Auld | |
| 9,681,793 B2 | 6/2017 | Artsyukhovich | |
| 10,012,800 B2 | 7/2018 | Diao | |
| 10,016,302 B2 | 7/2018 | Shazly | |
| 10,111,778 B2 | 10/2018 | Smith | |
| 10,245,181 B2 | 4/2019 | Diao | |
| 10,433,718 B2 | 10/2019 | Liolios | |
| 10,441,157 B2 | 10/2019 | Smith | |
| 2002/0045811 A1* | 4/2002 | Kittrell | G02B 6/4296 606/7 |
| 2004/0236183 A1 | 11/2004 | Durell | |
| 2006/0184162 A1 | 8/2006 | Smith | |
| 2008/0051770 A1 | 2/2008 | Scheller et al. | |
| 2008/0107384 A1 | 5/2008 | Nadolski | |
| 2008/0177257 A1 | 7/2008 | Smith et al. | |
| 2008/0215041 A1 | 9/2008 | Zemmouri | |
| 2008/0243108 A1 | 10/2008 | Murakami | |
| 2009/0270850 A1 | 10/2009 | Zhou | |
| 2009/0287196 A1 | 11/2009 | Zelickson | |
| 2009/0287197 A1 | 11/2009 | Hanley | |
| 2010/0027943 A1 | 2/2010 | Armani | |
| 2010/0261961 A1 | 10/2010 | Scott | |
| 2011/0122366 A1 | 5/2011 | Smith | |
| 2011/0144627 A1 | 6/2011 | Smith | |
| 2012/0191078 A1 | 7/2012 | Yadlowsky | |
| 2013/0150839 A1 | 6/2013 | Smith et al. | |
| 2014/0180264 A1* | 6/2014 | Diao | A61F 9/00821 606/4 |
| 2014/0194862 A1 | 7/2014 | Smith et al. | |
| 2014/0200566 A1 | 7/2014 | Smith | |
| 2014/0250668 A1 | 9/2014 | Smith | |
| 2015/0011839 A1* | 1/2015 | Auld | A61B 17/320016 600/249 |
| 2015/0351629 A1 | 12/2015 | Wheatley | |
| 2015/0366432 A1 | 12/2015 | Artsyukhovich | |
| 2016/0178844 A1 | 6/2016 | Griffin | |
| 2018/0055596 A1 | 3/2018 | Johnson | |
| 2018/0243136 A1 | 8/2018 | Diao | |
| 2018/0243137 A1 | 8/2018 | Diao | |
| 2018/0333304 A1 | 11/2018 | Diao | |
| 2018/0344528 A1 | 12/2018 | Farley | |
| 2019/0142544 A1 | 5/2019 | Horn | |
| 2019/0175217 A1 | 6/2019 | Cook | |
| 2019/0175273 A1 | 6/2019 | Cook | |
| 2019/0175404 A1 | 6/2019 | Cook | |
| 2019/0175405 A1 | 6/2019 | Diao | |
| 2019/0175406 A1 | 6/2019 | Cook | |
| 2019/0175407 A1 | 6/2019 | Bacher | |
| 2019/0175408 A1 | 6/2019 | Diao | |
| 2019/0209372 A1 | 7/2019 | Farley | |
| 2019/0307527 A1 | 10/2019 | Grueebler | |
| 2019/0365569 A1 | 12/2019 | Skovgaard | |
| 2020/0107960 A1 | 4/2020 | Bacher et al. | |

FOREIGN PATENT DOCUMENTS

| | | | |
|---|---|---|---|
| JP | 2013048864 A * | 3/2013 | |
| JP | 2013048864 A | 3/2013 | |
| WO | WO9208427 A2 | 9/1992 | |
| WO | WO0137769 A1 | 5/2001 | |
| WO | 2008024848 A2 | 2/2008 | |
| WO | 2008024848 A3 | 6/2008 | |
| WO | WO2018113887 A2 | 6/2018 | |

* cited by examiner

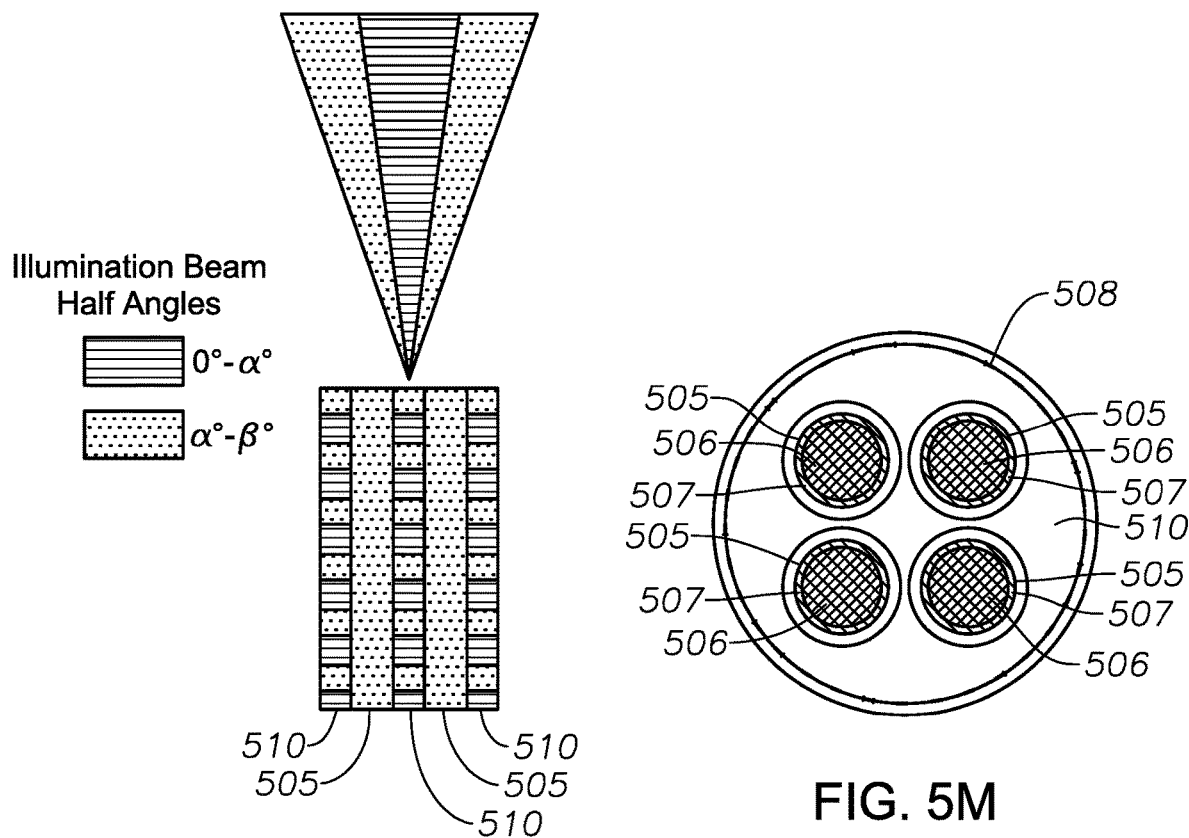
FIG. 5L
FIG. 5M
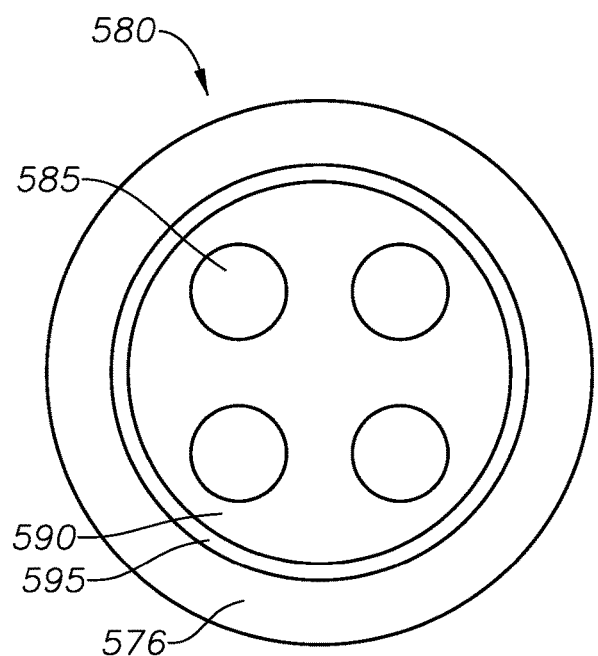
FIG. 5N

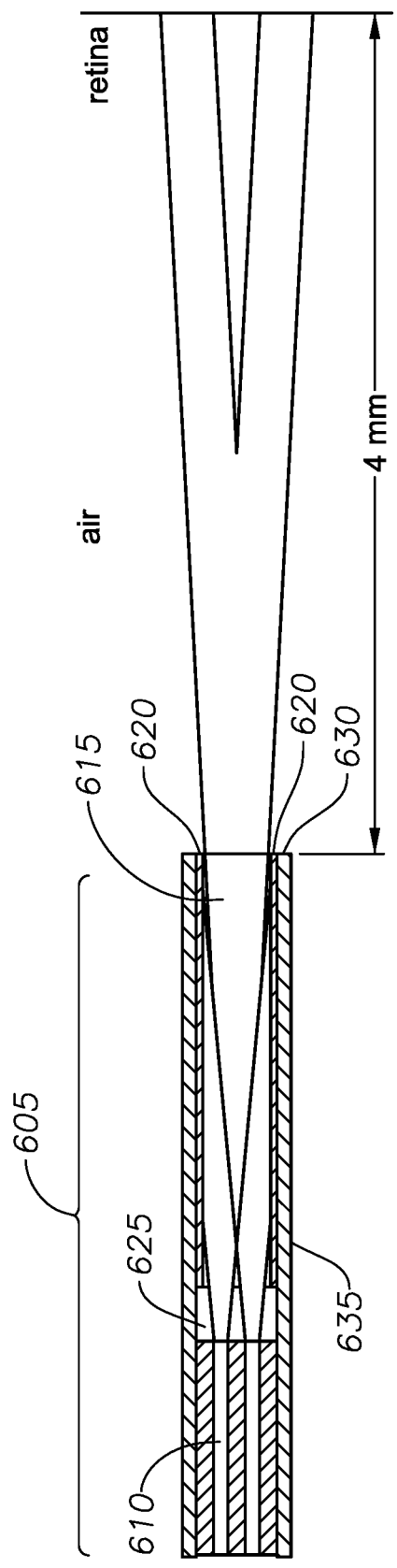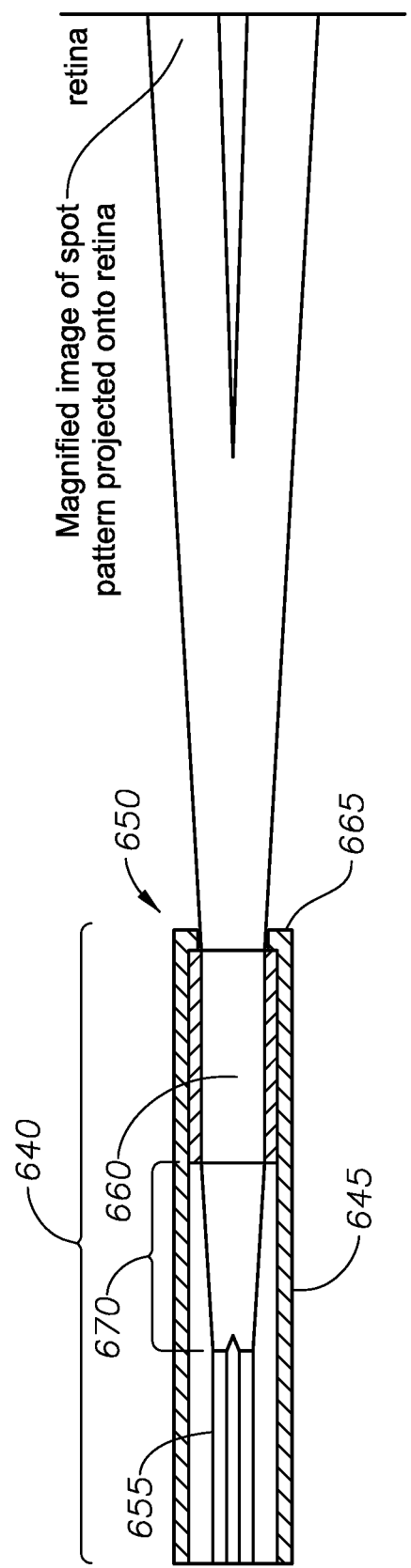
FIG. 6A
FIG. 6B

MULTIPLE-INPUT-COUPLED ILLUMINATED MULTI-SPOT LASER PROBE

PRIORITY CLAIM

This application claims the benefit of priority of U.S. Provisional Patent Application Ser. No. 62/598,653 titled "MULTIPLE-INPUT-COUPLED ILLUMINATED MULTI-SPOT LASER PROBE," filed on Dec. 14, 2017, whose inventors are Jochen Horn, Alireza Mirsepassi, and Ronald T. Smith, and U.S. Provisional Patent Application Ser. No. 62/597,550 titled "SURGICAL PROBE WITH SHAPE-MEMORY MATERIAL," filed on Dec. 12, 2017, whose inventors are Christopher Cook, Alireza Mirsepassi, and Kambiz Parto, which are hereby incorporated by reference in their entirety as though fully and completely set forth herein.

BACKGROUND

Field of the Disclosure

The present disclosure relates to a multiple-input-coupled illuminated multi-spot laser probe, and more specifically to systems and methods for creating multi-spot laser light beams, multiplexing an illumination light and the multi-spot laser light beams, and delivering the multiplexed light to a surgical handpiece via a multi-core optical fiber cable.

Description of Related Art

In many ophthalmic procedures a surgeon is required to use a variety of instruments in the patient's eye. For example, during a vitreoretinal surgery, a surgeon oftentimes manipulates a first handpiece for directing an illumination light beam onto the retinal surface in order to view patient anatomy and also manipulates an additional laser probe handpiece for delivering a laser treatment beam for treating the patient anatomy. However, there is a need for a multiple-input-coupled illuminated multi-spot laser probe.

SUMMARY

The disclosed embodiments of the present technology relates to multiple-input-coupled illuminated multi-spot laser probes, adaptors and other systems for multiplexing an illumination light and multi-spot laser light, and methods for multiplexing an illumination light and multi-spot laser light for and delivering the multiplexed light onto patient anatomy.

Some embodiments of the present technology involve a surgical laser system, an illumination light source, a surgical probe assembly, and a laser system port adaptor for creating a multi-spot pattern of laser light beams, multiplexing the multi-spot pattern of laser light beams with an illumination light beam, and delivering the multiplexed light beam to a surgical probe for simultaneously transmitting illumination light and a multi-spot pattern of laser light beams. The laser system port adaptor can include a first port arm for coupling with a laser source, a second port arm for coupling with an illumination system, a third port arm for coupling with a fiber optic cable of a laser probe, and a multiplexing intersection region. In some cases, the second port arm and the third port arm are substantially collinear across the intersection region, and the first port arm is substantially orthogonal to the second port arm and the third port arm at the multiplexing intersection region.

The intersection region of the laser system port adaptor can contain a diffractive optical element (DOE) configured to receive a collimated laser light beam from the optical element and to create a multi-spot laser pattern of laser light beams. In some cases, the DOE creates the multi-spot pattern of laser light beams as a 2×2 array pattern.

The intersection region can also contain a beamsplitter configured to reflect a plurality of narrow bands of the electromagnetic spectrum of light that correspond to the wavelengths of laser light emitted by the surgical laser system. The beamsplitter can further receive both the multi-spot pattern of laser light beams and an illumination beam from the illumination system. The beamsplitter can reflect the multi-spot laser pattern of laser light beams towards the third port arm and transmit portions of the illumination beam not contained within the at least two narrow bands of the electromagnetic spectrum towards the third port arm. In some cases, the second port arm includes a collimating lens for collimating the illumination light at the beamsplitter. Also, in some cases the intensity of the laser beams and the intensity of the illumination beam can be adjusted to produce a clear multiplexed multi-spot laser pattern of laser light beams and illumination beam.

The first port arm can include a ferrule having a diameter configured to securely couple within a female port of the laser source and can include an opening for allowing a focused laser spot from the laser source to enter the first port arm. The first port arm can also include an optical element for collimating a laser light beam. In some cases, the first port arm and the optical element have lengths configured to place the optical element substantially adjacent to the point of the focused laser spot from the laser source. Also, the first port arm can include external threading which, when tightened with a nut, couples the first port arm with the female port of the laser source and keeps the optical element substantially adjacent to the point of the focused laser spot from the laser source.

The third port arm can include a condensing lens substantially adjacent to the beamsplitter in the multiplexing intersection region. The condensing lens can be selected to focus the multi-spot laser pattern of laser light beams and the illumination beam onto an interface of the terminal end of a multi-core optical fiber cable of the surgical probe assembly.

The multi-core optical fiber cable can include a first outer core surrounded by an outer-core cladding and a plurality of inner cores contained within the outer core, each inner core in the plurality of inner cores surrounded by an inner-core cladding. In some cases, the plurality of inner cores contained within the outer core form a 2×2 array that matches a 2×2 multi-spot pattern of laser light beams from the DOE.

The materials for the various cores and the various claddings can be selected such that the focused illumination beam is propagated down an entire length of a first outer core of the multi-core optical fiber cable and such that each of the laser light beams in the multi-spot laser pattern of laser light beams is propagated down an entire length of one of a plurality of inner cores contained within the outer core.

In some cases, a refractive index of the outer core is greater than a refractive index of the outer-core cladding, a refractive index of each of the inner cores in the plurality of inner cores is greater than a refractive index of the inner-core cladding, and a refractive index of each or the inner cores in the plurality of inner cores is larger than the refractive index of the outer-core cladding. Further, the condensing lens can be selected to focus each of the laser beams in the multiplexed multi-spot pattern of laser light beams onto an interface with a respective inner core in the plurality of inner cores, wherein a spot size of each of the focused laser beams, an angular spread of each of the focused laser beams, a refractive index of the inner core, and a refractive index of the inner-core cladding causes the laser light beams to spatially fill and propagate through the plurality of inner cores for the length of the multi-core optical fiber cable.

Likewise, the condensing lens can be selected to focus the illumination beam as a light cone with a spot size to fall incident on at least a portion of the first outer core, at least a portion of the plurality of inner cores, and at least a portion of the inner-core claddings. The light cone of the illumination beam can include a narrow half-angle portion of the light cone and a wide half-angle portion of the light cone. In these cases, the refractive index for the various cores and claddings of the multi-core optical fiber cable and an angle of the narrow half-angle and wide half-angle portions of the light cone causes the illumination beam to spatially fill and propagate the length of the outer core of the multi-core optical fiber cable. Also, the narrow half-angle portion of the illumination beam can be confined within the outer core region, and the wide angle portion of the illumination beam is free to propagate within the outer core region, the inner cladding regions, and the inner core regions.

In some cases, the surgical probe assembly includes a ferrule for coupling with a laser system port adaptor or other multiplexing system. The surgical probe assembly can also include the multi-core fiber cable and a handpiece with a probe tip coupled with the distal end of the multi-core optical fiber cable. The probe tip can have a lens located substantially at a distal end of the probe tip and the multi-core optical fiber cable can terminate in an interface with the lens. The lens can be selected to translate the geometry of the multiplexed multi-spot laser pattern of laser light beams and illumination beam from the distal end of the multi-core optical fiber cable onto a target surface.

Some embodiments of the present technology involve methods of multiplexing a multi-spot pattern of laser light beams with an illumination light beam. The methods can involve directing a laser light beam to an optical element for collimating the laser light beam and directing the collimated laser light beam to a diffractive optical element (DOE) to create a multi-spot laser pattern of laser light beams. Likewise, the methods can involve directing the multi-spot pattern of laser light beams and an illumination light beam to a beamsplitter. Next, the method involves the beamsplitter reflecting the multi-spot pattern of laser light beams towards a condensing lens and transmitting the illumination light beam to the condensing lens, thereby multiplexing the multi-spot pattern of laser light beams and a transmitted illumination beam. The methods can also involve the condensing lens focusing the multiplexed multi-spot pattern of laser light beams and transmitted illumination beam onto an interface with a multi-core optical fiber cable. Also, the methods can involve directing the multiplexed multi-spot pattern of laser light beams and transmitted illumination beam through the multi-core optical fiber cable and onto a lens in a probe tip. Next, the lens translates a geometry of the multiplexed multi-spot laser pattern of laser light beams and illumination beam from the distal end of the multi-core optical fiber cable onto a target surface.

Some embodiments of the present technology involve methods of creating an image of a multiplexed beam of multi-spot pattern of laser light beams and illumination light. The methods can involve selecting, for a multi-core optical fiber cable, a material with a first refractive index for an outer core, a material with a second refractive index for an outer-core cladding, a material with a third refractive index for a plurality of inner cores contained in the outer core, and a material with a fourth refractive index for an inner-core cladding for each of the plurality of inner cores. The methods can also include determining a numerical aperture of laser light beams from a laser source and a numerical aperture of an illumination light beam from an illumination light source, and selecting a condensing lens to focus the multiplexed multi-spot pattern of laser light beams and illumination beam onto an interface plane of the multi-core optical fiber cable. Next, the methods can include multiplexing a multi-spot pattern of laser light beams with the illumination light beam and focusing the multiplexed multi-spot pattern of laser light beams and illumination beam onto an interface plane of the multi-core optical fiber cable such that the illumination beam propagates down the outer core and the laser beams propagate down the multiple inner cores. The methods can also involve directing the multiplexed beam of multi-spot pattern of laser light beams and illumination light through a lens in the surgical handpiece.

Some embodiments of the present technology involve an integrated illumination and multi-spot laser multiplexing system. The integrated system can include a laser source that emits a collimated laser light beam and a diffractive optical element (DOE) configured to receive the collimated laser light beam and to create a multi-spot laser pattern. The integrated system also includes an illumination system that emits substantially white light and a collimating lens that collimates the substantially white light received from the illumination system. The integrated system further includes a fiber optic cable port that couples a multi-core optical cable fiber to the system and a beamsplitter that reflects the multi-spot laser pattern towards a condensing lens and that transmits the collimated illumination beam towards the condensing lens, thereby multiplexing the multi-spot laser light beams and the illumination light beam. The condensing lens can further focus the multiplexed multi-spot pattern of laser light beams and illumination beam onto an interface with the fiber optic cable port, through a multi-core optical fiber cable, and onto a lens in the tip of a surgical handpiece that translates a geometry of the multiplexed multi-spot laser pattern of laser light beams and illumination beam onto a target surface.

Some embodiments of the present technology involve an integrated illumination and multi-spot laser multiplexing system. The system can include a laser source that emits a collimated laser light beam, a diffractive optical element (DOE) to create a multi-spot laser pattern of laser light, an illumination system that emits substantially white light, and a collimating lens that collimates the substantially white light received from the illumination system. The system further includes a beamsplitter that reflects the collimated laser light beam and that transmits the collimated illumination beam towards a condensing lens. The DOE creates a multi-spot laser pattern of laser light beams and the beamsplitter multiplexes the pattern of laser light beams and the illumination light beam. The system further includes a fiber optic cable port that couples the multiplexed light with a multi-core optical cable fiber.

BRIEF DESCRIPTION OF THE DRAWINGS

For a more complete understanding of the present technology, its features, and its advantages, reference is made to the following description, taken in conjunction with the accompanying drawings, in which:

FIGS. 5F-5M illustrate the propagation of the multiplexed light through a multi-core optical fiber cable in accordance with a particular embodiment of the present disclosure;

FIG. 6A-6B illustrate an open side views of tips of a surgical hand probe in accordance with a particular embodiment of the present disclosure;

DESCRIPTION

In a wide variety of medical procedures, laser light is used to assist the procedure and treat patient anatomy. For example, a vitreoretinal surgery oftentimes involves using a laser treatment beam for photocoagulation of retinal tissue. Vitreoretinal procedures commonly involve a laser probe that is capable of alternately emitting an aiming laser beam to select target spots on retinal tissue and emitting a treatment laser beam to perform the photocoagulation at the targeted spots. Frequently, the laser probe utilizes light in a red band of the electromagnetic spectrum for the aiming beam and light in a green band of the electromagnetic spectrum for the treatment beam. Also, during a panretinal laser photocoagulation procedure, a surgeon selects thousands of spots on retinal tissue to apply the treatment laser beam to, resulting in a very long and tedious procedure. Therefore, a laser probe capable of producing a multi-spot pattern of laser light is desirable.

Vitreoretinal procedures also benefit from illumination light being directed into the eye and onto retinal tissue. Vitreoretinal surgeons oftentimes use a laser probe handpiece for delivering the laser aiming and treatment beams and also use an additional handpiece for directing an illumination light beam onto the retinal surface in order to view patient anatomy.

The field of vitreoretinal surgery, as well as other medical laser procedures, would benefit from multiplexing an illumination light and multi-spot laser light. Accordingly, the technology described herein involves multiple-input-coupled illuminated multi-spot laser probes, adaptors and other systems for multiplexing an illumination light and multi-spot laser light, and methods for multiplexing an illumination light and multi-spot laser light and delivering the multiplexed light onto patient anatomy.

Figure 1:
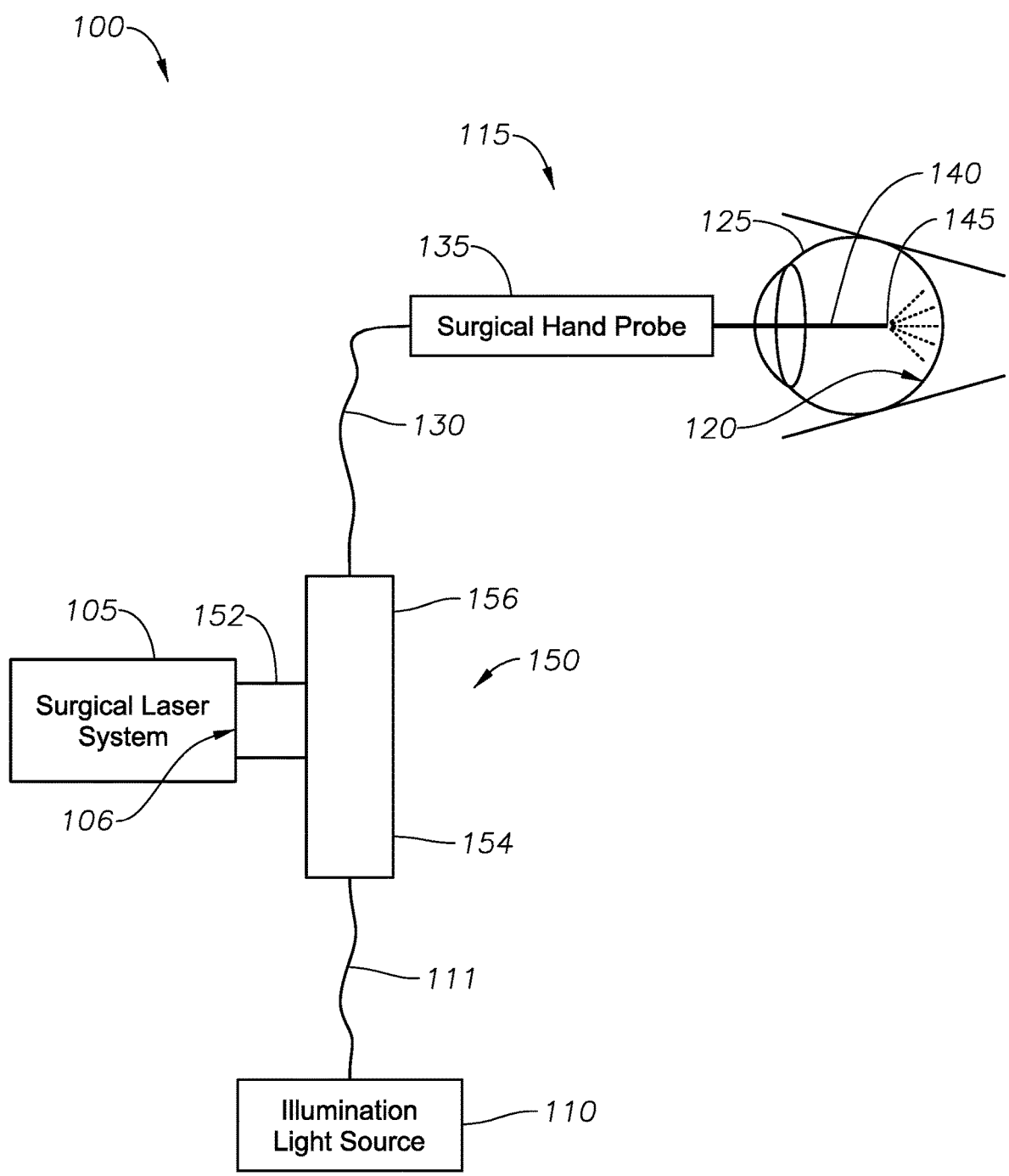
FIG. 1 illustrates a system for creating a multi-spot pattern of laser light beams, multiplexing the multi-spot pattern of laser light beams with an illumination light beam, and delivering the multiplexed light beam to a surgical probe in accordance with a particular embodiment of the present disclosure.

FIG. 1 illustrates a system 100 for creating a multi-spot pattern of laser light beams, multiplexing the multi-spot pattern of laser light beams with an illumination light beam, and delivering the multiplexed light beam to a surgical probe 115 for simultaneously transmitting illumination light and a multi-spot pattern of laser light beams in accordance with a particular embodiment of the present disclosure.

The system 100 includes a surgical laser system 105 that includes one or more laser sources for generating laser beams used during an ophthalmic procedure. For example, the ophthalmic surgical laser system 105 can alternatively generate a surgical treatment beam with a wavelength of around 532 nanometers (nm) and a laser aiming beam with a wavelength of around 635 nm. A surgeon or surgical staff member can control the surgical laser system 105 (e.g., via a foot switch, voice commands, etc.) to alternatively emit the laser aiming beam and fire the treatment beam to treat patient anatomy (e.g., perform photocoagulation). The laser beams can be emitted through a port 106 in the surgical laser system 105.

The system 100 also includes an illumination light source 110 that can include one or more of a xenon illumination, an RGB light-emitting diode (LED) illuminator, a white light LED illuminator, a laser-pumped phosphor illuminator, a supercontinuum white laser illuminator, etc. The illumination light source 110 can be a surgical console that can monitor and control a wide variety of aspects of an ophthalmic procedure. For example, the surgical console can be configured for use in vitreoretinal surgery and can power and control vitrectomy probes, can integrate pressurized infusion delivery and intraocular pressure compensation, can provide surgical illumination, etc. In some cases, the illumination light source 110 can deliver the illumination light via an illumination cable 111.

The system 100 also includes a laser system port adaptor 150 containing optical elements (not shown) for creating a multi-spot pattern of laser light beams from a laser light beam from the ophthalmic surgical laser system 105 and multiplexing the multi-spot pattern of laser light beams with an illumination light beam received from the illumination light source 110. The adaptor 150 can include a plurality of port arms 152, 154, 156 that couple with the surgical laser source 105, the illumination light source 110, and to the surgical probe 115, respectively.

The system 100 can deliver the multiplexed light beam from the port arm 156 to the surgical probe 115 via a multi-core optical fiber cable 130 to provide the surgical probe 115 the ability of simultaneously providing illumination light and a multi-spot pattern of laser light beams to the retina 120 of a patient's eye 125. The surgical probe 115 includes a probe body 135 and a probe tip 140 that house and protect the multi-core optical fiber cable 130. A distal end 145 of the probe tip 140 also contains a lens (not shown, described in greater detail below) that translates the multiplexed light beam from the distal end of the multi-core optical fiber cable onto the retina 120.

Figure 2A:
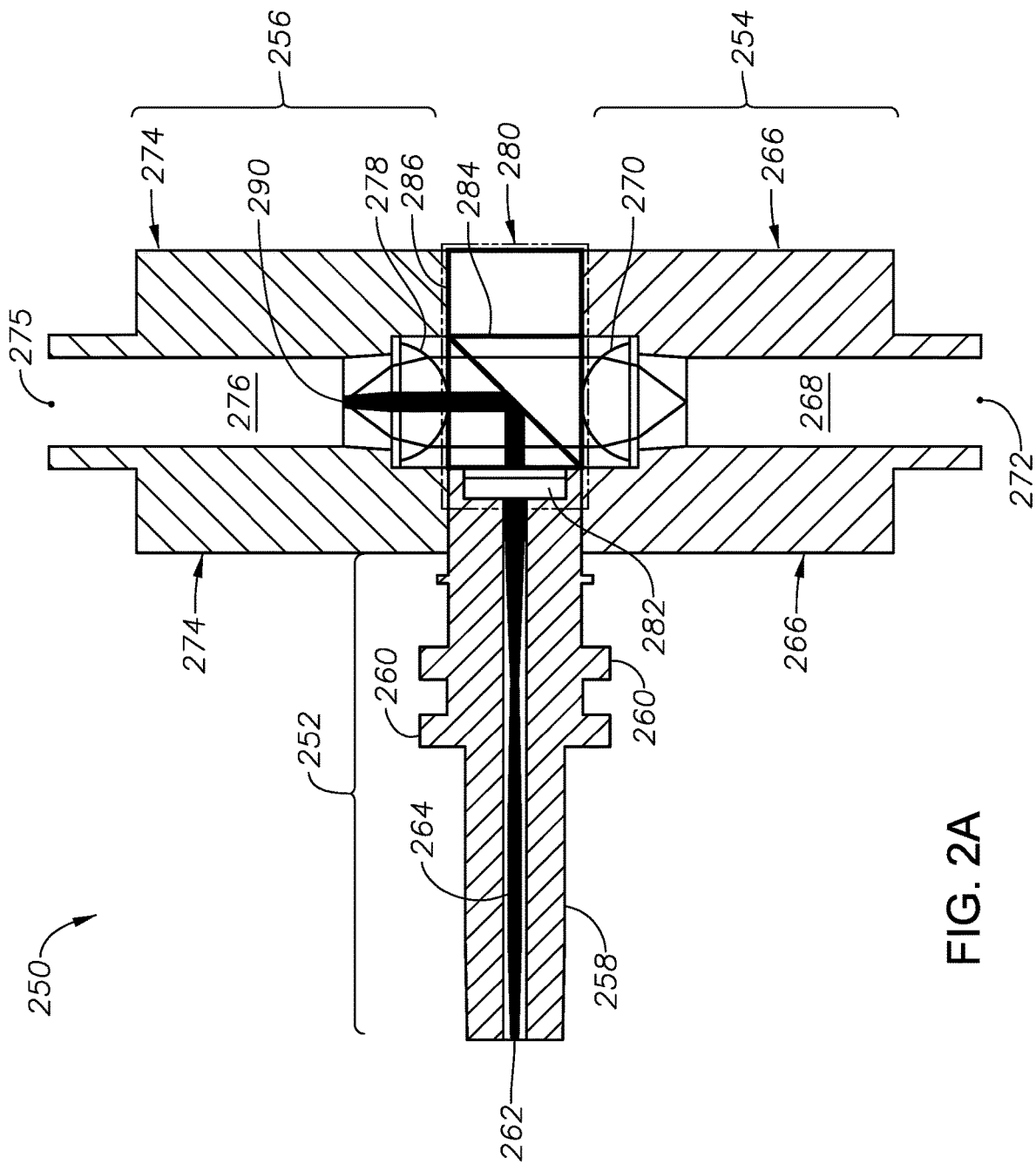
FIG. 2A illustrates a laser system port adaptor in accordance with a particular embodiment of the present disclosure.

As disclosed herein, various systems and methods can be employed for creating a multi-spot pattern of laser light beams multiplexing the multi-spot pattern of laser light beams with an illumination light beam. As briefly mentioned above, in some cases, a port adaptor can contain optical elements for creating a multi-spot pattern and multiplexing light beams. FIG. 2A illustrates a laser system port adaptor 250 according to some embodiments of the present disclosure. The laser system port adaptor 250 includes a first port arm 252 for coupling with a laser source, a second port arm 254 for coupling with an illumination system, and a third port arm 256 for coupling with a fiber optic cable of a laser probe. The laser system port adaptor 250 also includes a multiplexing intersection region 280 where the first port arm 252, the second port arm 254, and the third port arm 256 intersect. In some cases, the second port arm 254 and the third port arm 256 are substantially collinear across the multiplexing intersection region 280, and the first port arm 252 is substantially orthogonal to the second port arm 254 and the third port arm 256 at the multiplexing intersection region 280.

The first port arm 252 includes a ferrule 258 that functions as a male coupling for a female chimney port (not shown) of the laser system. The ferrule 258 has an opening 262 that allows laser light from the laser source to enter the first port arm 252. Also, the ferrule 258 can house an optical element 264 contained within the ferrule 258. The optical element 264 is configured to collimate laser light received from the laser source. For example, the optical element 264 can be a graded-index (GRIN) lens with a length and a pitch selected such that the optical element 264 collimates laser light received at the opening 262 at a selected distance adjacent to a diffractive optical element (DOE) 282 contained within the multiplexing intersection region 280, as described in more detail below.

The first port arm 252 also includes an external threading 260 to draw the first port arm substantially all the way into the female port of the surgical laser system 105 when a nut is tightened on the external threading. In some cases, the optical element 264 is positioned within the ferrule 258 that is flush with the opening 262, and the surgical laser system 105 is configured to focus a laser spot at the terminal end of the female port. Accordingly, the external threading 260 can facilitate the optical element 264 being positioned at a point relative to the surgical laser system 105 such that a focused laser spot of a laser produced by the surgical laser system falls substantially incident onto the end of the optical element 264.

The second port arm 254 for coupling with an illumination system can comprise a female port having a substantially cylindrical external frame 266, an internal cavity 268, a collimating lens 270 at a first end of the internal cavity 268, and an opening 272 at the second end of the internal cavity 268. The internal cavity 268 of the second port arm 254 can be configured to receive a ferrule of an optical cable 111 that delivers an illumination light beam from the illumination light source 110. In some cases, the ferrule of the optical cable that delivers an illumination light beam is secured to the second port arm 254 with a nut such that the illumination emitted from an optical fiber contained within the optical cable spreads to fall incident onto the collimating lens 270 such that the collimating lens 270 delivers substantially collimated illumination light to a beamsplitter 284 contained in the multiplexing intersection region 280.

The third port arm 256 for coupling with a fiber optic cable of a laser probe can comprise a female port having a substantially cylindrical external frame 274, an internal cavity 276, a condensing lens 278 at a first end of the internal cavity 276, and an opening 275 at the second end of the internal cavity 276.

The internal cavity 276 of the third port arm 256 can be configured to receive a ferrule of a multi-core optical fiber cable 130 that delivers multiplexed light to the surgical probe 115, as explained in greater detail below. In some cases, the ferrule of a multi-core optical fiber cable is secured to the third port arm 256 with a nut such that the condensing lens 278 precisely focuses the multiplexed light onto an interface 290 of the terminal end of the multi-core optical fiber cable such that an illumination beam and laser aiming/treatment beams are propagated down an entire length of the multi-core optical fiber cable, as explained in greater detail below.

As explained above, the laser system port adaptor 250 also includes a multiplexing intersection region 280 where the first port arm 252, the second port arm 254, and the third port arm 256 intersect. The multiplexing intersection region can contain a diffractive optical element (DOE) 282 configured to receive a collimated laser light beam from the optical element 264 of the first port arm 252 and to create a multi-spot laser pattern of laser light beams. The DOE 282 can be selected to diffract incident laser light into a multi-spot pattern that will align with an intended target geometry. For example, the DOE 282 can be selected to create a 2×2 array pattern of laser light beams that substantially matches a 2×2 array of inner cores of a multi-core optical fiber cable that delivers the multiplexed light to the surgical probe 115, as explained in greater detail below.

The multiplexing intersection region 280 also contains a beamsplitter 284 configured to reflect a portion of the light spectrum and transmit a remaining portion of the light spectrum. More specifically, the beamsplitter 284 can be configured to both: a) reflect laser aiming and treatment beams from the surgical laser system 105 toward the third port arm 256 and the condensing lens 278, and b) transmit the illumination light from the illumination light source 110 toward the third port arm 256 and the condensing lens 278. Also, as mentioned above, the condensing lens 278 can be selected to precisely focus the multiplexed light onto an interface 290 of the terminal end of the multi-core optical fiber cable 130 such that an illumination beam and laser aiming/treatment beams are propagated down an entire length of the multi-core optical fiber cable 130, as explained in greater detail below.

As explained above, vitreoretinal procedures frequently utilize light in a red band of the electromagnetic spectrum for a laser aiming beam and light in a green band of the electromagnetic spectrum for a laser treatment beam. Accordingly, the beamsplitter 284 can be configured to highly reflect light in a narrow band of the red spectrum and a narrow band of the green spectrum and configured to transmit the remaining electromagnetic spectrum. In some embodiments, the beamsplitter 284 reflects light in a first narrow band around 532 nanometers (nm) and in a second narrow band around 635 nm and transmits the remaining spectrum. The beamsplitter 284 can be a dichroic beamsplitter cube, a beamsplitter plate, etc.

Since portions (e.g., red and green portions) of the illumination light from the illumination light source 110 are reflected by the beamsplitter 284, the system port adaptor 250 can include a light collection module 286. For example, the light collection module 286 can be a beam dump, power monitor, etc.

Figure 2B:
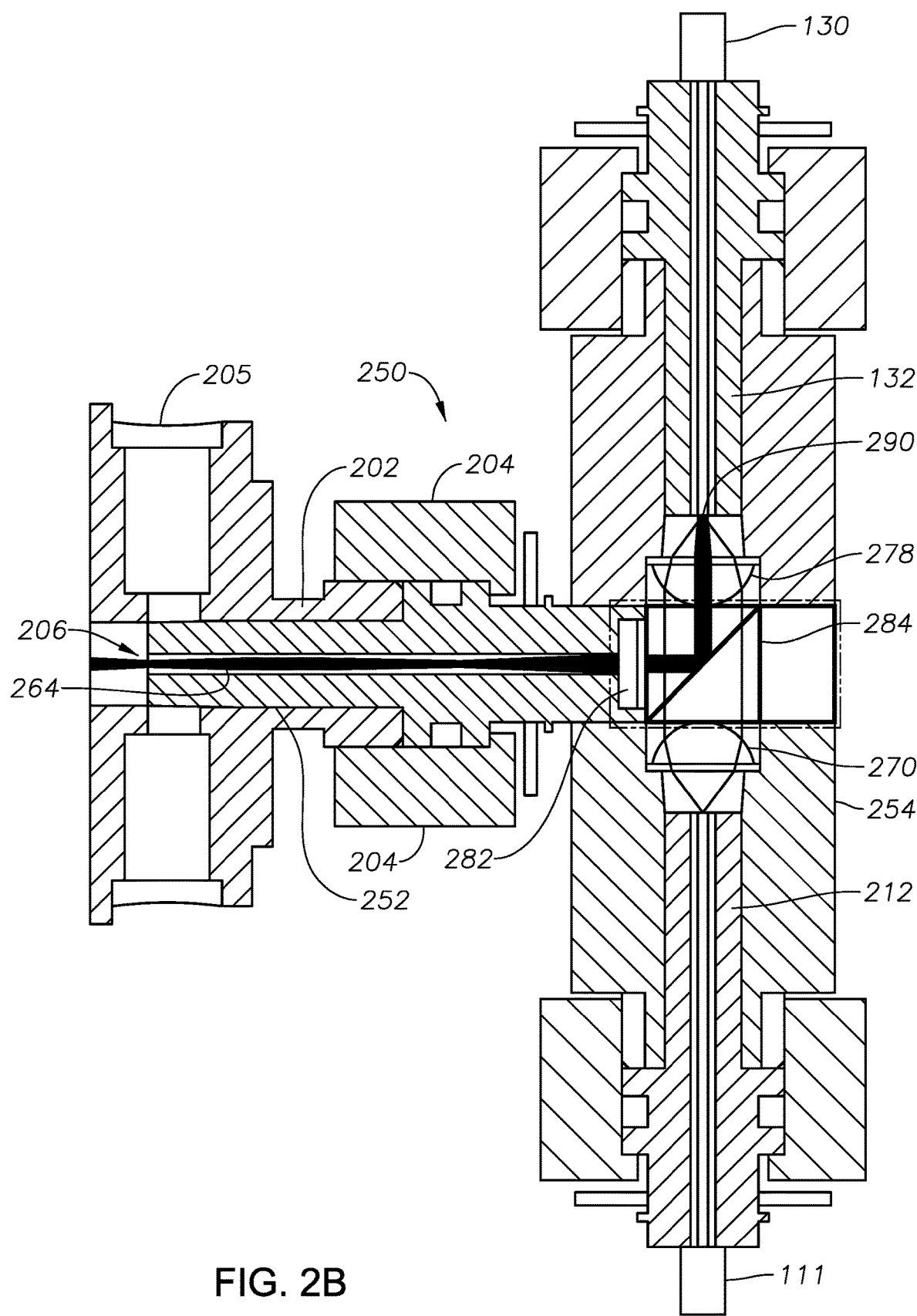
FIG. 2B illustrates the laser system port adaptor coupled with a surgical laser system and an illumination light source in accordance with a particular embodiment of the present disclosure.

FIG. 2B illustrates the laser system port adaptor 250 coupled with a surgical laser system 205, a ferrule 212 of an optical cable 111 that delivers an illumination light beam from the illumination light source 110, and a ferrule 132 of the multi-core optical fiber cable 130 that delivers multiplexed light to the surgical probe 115.

The surgical laser system 205 includes a female port 202 with an opening 206 in the proximal end of the female port 202 that allows laser light to exit the surgical laser system 202. The female port 202 is configured to receive the first port arm 252 of the laser system port adaptor 250 such that the optical element 264 in the first port arm 252 is substantially adjacent to the opening 206. The surgical laser system 205 is configured to focus laser light substantially onto an interface plane at the opening 206 and the optical element 264. Also, a nut 204 can be used to secure the laser system port adaptor 250 with the surgical laser system 205 and maintain the proximity of the optical element 264 with the opening 206 in the female port 202.

As explained above, an ophthalmic surgical laser system 105 can alternatively generate a surgical treatment beam with a wavelength of around 532 nanometers (nm) (i.e., green) and a laser aiming beam with a wavelength of around 635 nm (i.e., red). However, red and green incident laser light diffract off a DOE with different diffraction angles. When the laser beams are not collimated then their focus is also affected, i.e. red and green will focus at different axial locations. This greatly complicates trying to focus both green and red laser beams into the same inner-core regions of the multi-core fiber, as explained in greater detail below. Therefore, some embodiments involve collimating the multiple beams that fall incident on the DOE so that the multiple beams generated from the DOE are also collimated. To achieve a multi-spot laser pattern with sufficient focus, the laser light from the surgical laser system 205 should be collimated when it falls incident on the DOE 282. Therefore, in some cases, the optical element 264 can selected to be long enough (e.g., 16.54 mm) to collimate laser light from the surgical laser system 205, bring the laser light back into focus, and collimate the laser light a second time such that the laser light is collimated at the DOE 282.

In some cases, the optical element 264 is a 0.75 pitch, 0.20 NA GRIN relay lens that receives laser focused input beam and outputs a collimated beam at the distal end of the GRIN lens. The GRIN lens is long enough to collimate the beam then bring it to a focus and then collimate is a second time. In some other cases, the optical element 264 is a refractive-lens relay system.

The DOE 282 receives the collimated laser light and creates a multi-spot pattern of laser light beams. For example, in some cases, the DOE 282 can create a 2×2 array pattern of laser light beams that substantially matches a 2×2 array of inner cores of the multi-core optical fiber cable 130 that delivers the multiplexed light to the surgical probe 115, as explained in greater detail below. In some other cases, the DOE 282 can be replaced by an assembly of prisms and/or beamsplitters to create the multi-spot pattern of laser light beams.

As also shown in FIG. 2B, the second port arm 254 of the laser system port adaptor 250 is also coupled with a ferrule 212 of an optical cable 111 that delivers an illumination light beam from the illumination light source 110. In some cases, the length of the internal cavity of the second port arm 254 is selected such that a terminal end of an optical fiber contained within the optical cable 111 is positioned a predetermined distance from the collimating lens 270. The collimating lens 270 and/or the predetermined distance of the optical fiber from the collimating lens 270 can be selected such that the illumination light is substantially fully collimated at the beamsplitter 284. Also, a nut can secure the ferrule 212 in the internal cavity 268 and maintain the predetermined distance of the optical fiber 218 from the collimating lens 270.

Also, as mentioned above, the beamsplitter 284 can be configured to both: a) reflect laser aiming and treatment beams from the surgical laser system 105 toward the third port arm 256 and the condensing lens 278, and b) transmit the illumination light from the illumination light source 110 toward the third port arm 256 and the condensing lens 278.

As also shown in FIG. 2B, the third port arm 254 of the laser system port adaptor 250 is coupled with a ferrule 132 of the multi-core optical fiber cable 130 that delivers multiplexed light to the surgical probe 115. Also, the condensing lens 278 can be selected to precisely focus the multiplexed light onto an interface 290 of the terminal end of the multi-core optical fiber cable 130 such that an illumination beam and laser aiming/treatment beams are propagated down an entire length of the multi-core optical fiber cable 130, as explained in greater detail below.

Figure 3:
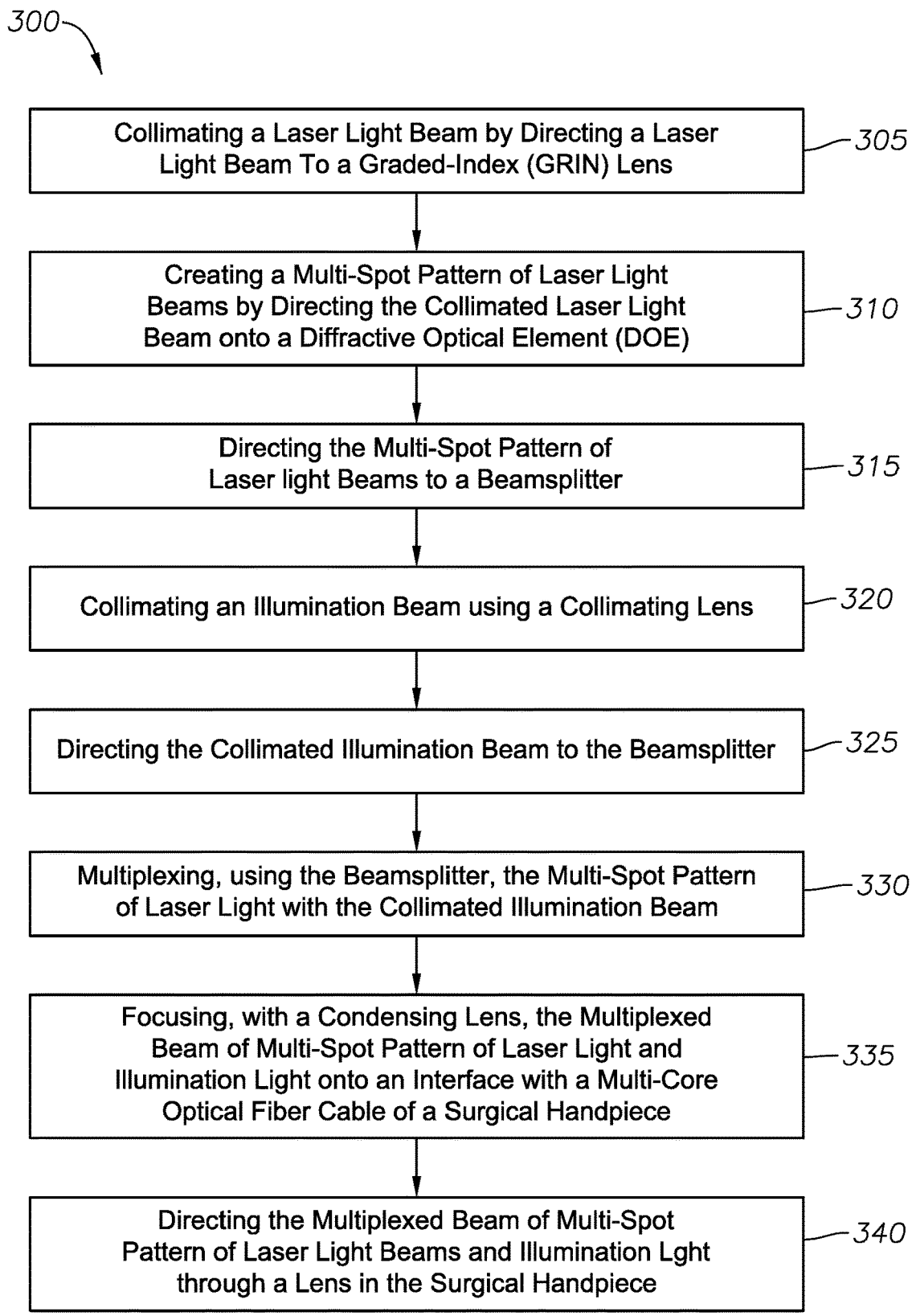
FIG. 3 illustrates a method for multiplexing a multi-spot pattern of laser light beams and illumination light in accordance with a particular embodiment of the present disclosure.

FIG. 3 illustrates a method 300 for multiplexing a multi-spot pattern of laser light beams and illumination light in accordance with a particular embodiment of the present disclosure. The method 300 involves collimating a laser light beam by directing a laser light beam to a graded-index (GRIN) lens at step 305, creating a multi-spot pattern of laser light beams by directing the collimated laser light beam onto a diffractive optical element (DOE) at step 310, and directing the multi-spot pattern of laser light beams to a beamsplitter at step 315.

The method 300 also involves collimating an illumination beam using a collimating lens at step 320 and directing the collimated illumination beam to the beamsplitter at step 325. Next, the method 300 involves multiplexing, using the beamsplitter, the multi-spot pattern of laser light with the collimated illumination beam at step 330. More specifically, in some cases, multiplexing the multi-spot pattern of laser light with the collimated illumination beam can involve the beamsplitter reflecting laser aiming and treatment beams from the surgical laser system toward a condensing lens and transmitting the illumination light from the illumination light source towards the condensing lens.

The method 300 also involves focusing, with a condensing lens, the multiplexed beam of multi-spot pattern of laser light and illumination light onto an interface with a multi-core optical fiber cable of a surgical handpiece at step 335 and, subsequently, directing the multiplexed beam of multi-spot pattern of laser light beams and illumination light through a lens in the surgical handpiece at step 340, as described in more detail below.

In some cases, the intensities of the white illumination and the laser aiming beams can be adjusted (e.g., at the illumination light source and surgical laser system, respectively) to provide the right amount of laser aiming beam contrast against the white while providing enough white illumination to easily see the retina.

The system 100 illustrated in FIG. 1 and described herein involves a modular approach with a separate surgical laser system and illumination light source. However, in some cases, the surgical laser system and illumination light source can be integrated in a single module and the module can contain the appropriate optics for creating a multi-spot pattern of laser light beams, multiplexing the multi-spot pattern of laser light beams with an illumination light beam, and delivering the multiplexed light beam to a surgical probe for simultaneously transmitting illumination light and a multi-spot pattern of laser light beams.

Figure 4A:
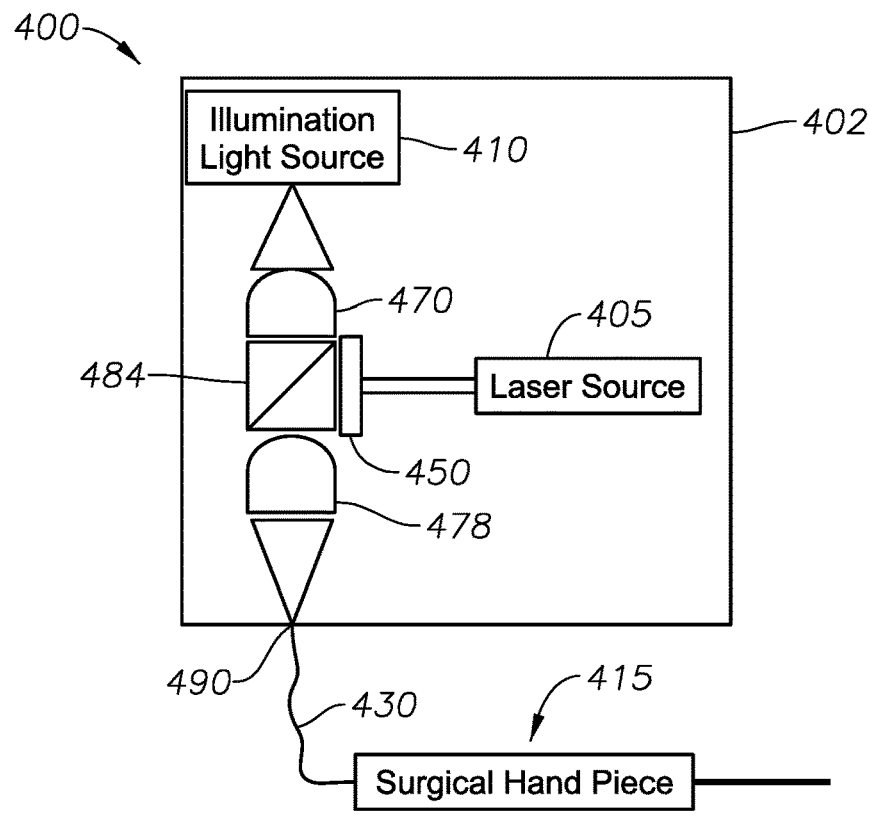
FIG. 4A-4B illustrate systems including a light multiplexing component containing a laser source and an illumination light source in accordance with a particular embodiment of the present disclosure.

FIG. 4A illustrates a system 400 that includes a light multiplexing component 402 containing a laser source 405 and an illumination light source 410 in accordance with a particular embodiment of the present disclosure. The laser source can generate substantially collimated laser beams (e.g., red aiming beams, green treatment beams) and direct the laser beams towards a beamsplitter 484. Also, a linear slide 450 (or rotating wheel) can be positioned in the beam path between the laser source 405 and the beamsplitter 484. The linear slide 450 can include multiple optical features that can be alternatively slid into the beam path between the laser source 405 and the beamsplitter 484. For example, the linear slide 450 can include a diffractive optical element (DOE) that creates a multi-spot pattern of laser light beams and a clear window or a hollow section that allows the laser light to pass through unaffected, resulting in a single spot laser beam.

The illumination light source 410 can be a white LED, an RGB LED, a xenon laser, a pumped phosphor laser, discreet lasers, supercontinuum laser, etc. The illumination light source can generate and direct illumination light to a collimating lens 470 and towards the beamsplitter 484.

The beamsplitter 484 can be configured to both reflect laser aiming and treatment beams from the laser source 405 toward a condensing lens 478 and transmit the collimated illumination light from the illumination light source 410 toward the condensing lens 478. The condensing lens 478 can be selected to precisely focus the multiplexed light onto an interface 490 of the terminal end of the multi-core optical fiber cable 430 such that an illumination beam and laser aiming/treatment beams are propagated down an entire length of the multi-core optical fiber cable 430 and into a surgical hand piece 415, as explained in greater detail below.

Figure 4B:
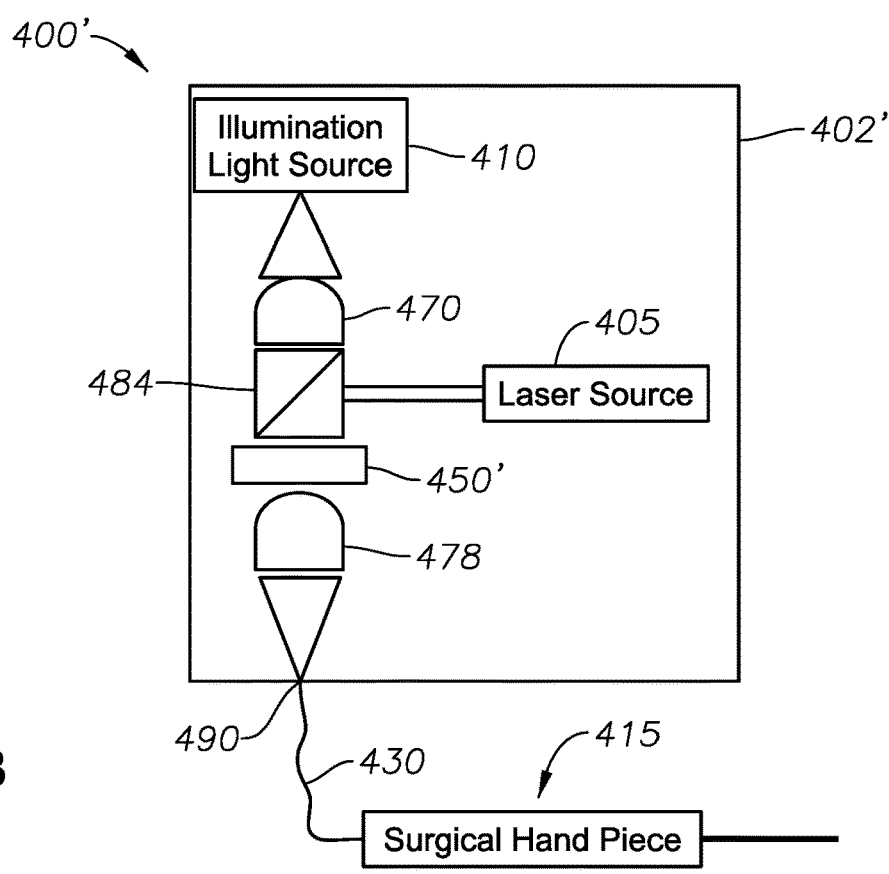

FIG. 4B illustrates another system 400' that includes a light multiplexing component 402' containing a laser source 405 and an illumination light source 410. Here, the beamsplitter 484 can multiplex laser light from the laser source 405 and collimated illumination light from the illumination light source 410 before the multiplexed light beam falls incident on a rotating wheel 450'. When the rotating wheel 450 positions a DOE into the beam path, the DOE can create a multi-spot pattern of laser light beams within the illumination light. Also, the system 400' can include a condensing lens 478 to focus the multiplexed light beam onto an interface 490 of the terminal end of the multi-core optical fiber cable 430

Figure 4C:
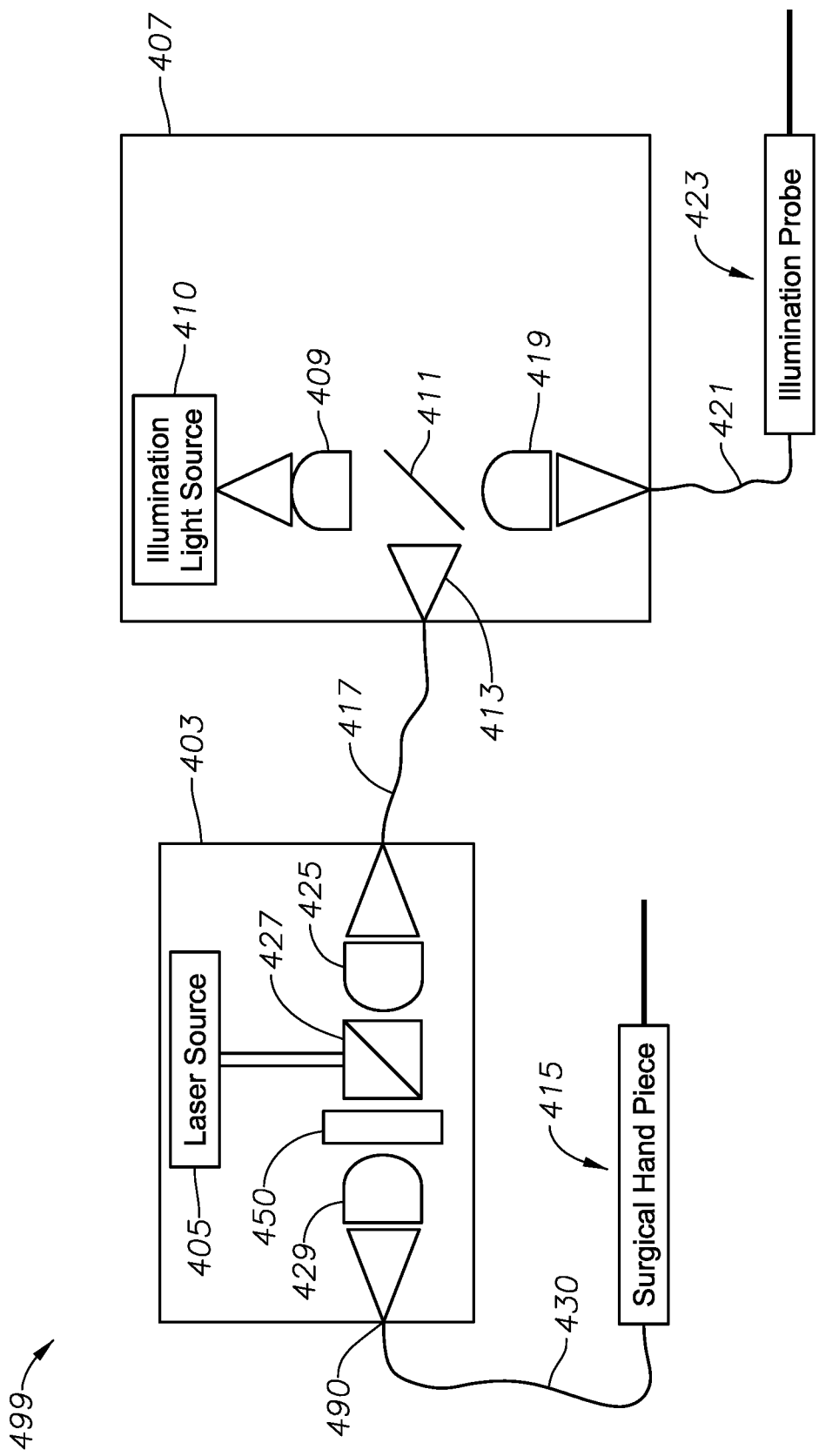
FIG. 4C illustrates a system that includes a laser light multiplexing module containing a laser source and an illumination module that includes an illumination light source in accordance with a particular embodiment of the present disclosure.

FIG. 4C illustrates another system 499 in accordance with a particular embodiment of the present disclosure that includes a laser light multiplexing module 403 containing a laser source 405 and an illumination module 407 that includes an illumination light source 410. The illumination module 407 includes a collimating lens 409 that collimates light from the light source 410 and a slidable mirror 411 that can be alternatively positioned into and out of the beam path of collimated light from the collimating lens 409. When the slidable mirror 411 is positioned within the beam path of collimated light from the collimating lens 409, the slidable mirror directs the collimated light to a fiber optic coupling 413 and into a fiber optic delivery cable 417. When the slidable mirror 411 is positioned out of the beam path of collimated light from the collimating lens 409, the collimated light is directed to a condensing lens 419 that focuses the light into a fiber optic cable 421 that is coupled to an illumination probe 423 used for delivery of purely illumination light.

The fiber optic delivery cable 417 delivers the illumination light from the illumination module to a collimating lens 425 in the laser light multiplexing module 403. The collimating lens 425 collimates the illumination light and directs the collimated light to a beamsplitter 427. Also, the laser source 405 directs substantially collimated (i.e., substantially collimated due to the substantially point-source nature of the laser light from the laser light source 405) to the beamsplitter 427. The beamsplitter 427 is configured to transmit a portion of the light spectrum that corresponds to the wavelengths emitted by the laser source (e.g., red and green laser light) and configured to reflect a remaining portion of the light spectrum. More specifically, the beamsplitter 427 can be configured to both reflect laser aiming and treatment beams from the laser source 405 and transmit the illumination light from the collimating lens 425. In this configuration the beamsplitter 427 effectively multiplexes laser light from the laser source 405 and collimated illumination light from the illumination light source 410. The multiplexed light beam falls incident on a linear slide 450 that alternatively positions a DOE into the beam path to create a multi-spot pattern of laser light beams within the illumination light. Also, the laser light multiplexing module 403 includes a condensing lens 429 to focus the multiplexed light beam onto an interface 490 of the terminal end of the multi-core optical fiber cable 430 for delivery to surgical hand piece 415.

In some cases, the light multiplexing components 402, 402' and/or the laser light multiplexing module 403 are also integrated into a surgical console that include means for controlling aspects of a surgical procedure. For example, the light multiplexing components 402, 402' and/or the laser light multiplexing module 403 can be integrated within a surgical console configured for use in vitreoretinal surgery that can power and control vitrectomy probes, can integrate pressurized infusion delivery and intraocular pressure compensation, can provide surgical illumination, etc. Also, in some cases, the light multiplexing components 402, 402' and/or the laser light multiplexing module 403 are a stand-alone modules that can be used alongside a surgical console.

As mentioned above, a condensing lens can be selected to precisely focus the multiplexed light onto an interface of the terminal end of the multi-core optical fiber cable such that an illumination beam and laser aiming/treatment beams are propagated down an entire length of the multi-core optical fiber cable and into a surgical hand probe. More specifically, the condensing lens can be selected such that resulting light cones of light from the illumination beam and laser aiming/treatment beams have an acceptance angle and a numerical aperture (NA) to interface with the various fiber core and cladding materials used in the multi-core optical fiber cable such that the illumination beam and the laser aiming/treatment beams are propagated down the appropriate core fibers the entire length of the multi-core optical fiber cable.

Figure 5A:
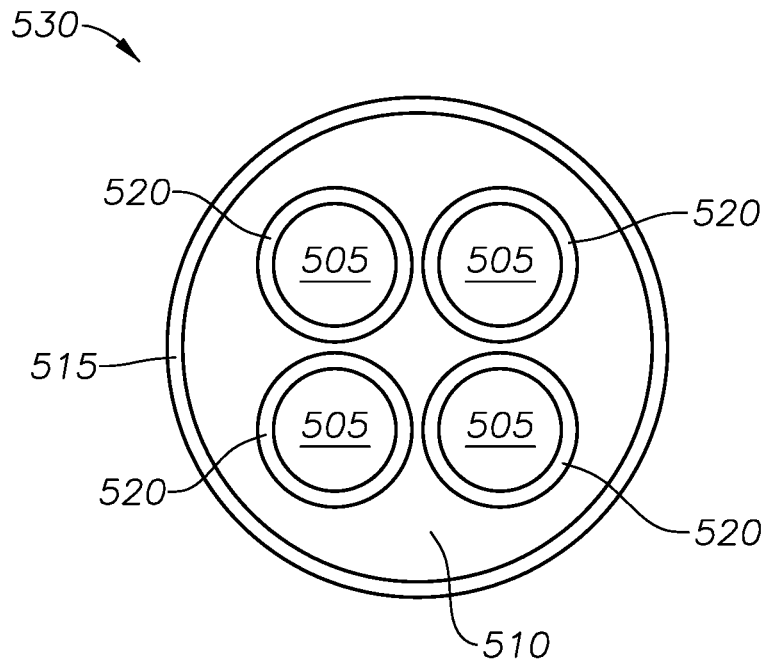
FIG. 5A illustrates the top view of a terminal end of a multi-core optical fiber cable in accordance with a particular embodiment of the present disclosure.

FIG. 5A illustrates the top view of a proximal end of a multi-core optical fiber cable 530 according to some embodiments of the present disclosure. The multi-core fiber cable 530 can include four inner core fibers 505 with a relatively small-diameter and a relatively small NA inside of an outer core fiber 510 having a relatively large diameter and a relatively large NA. The outer core fiber 510 can be contained within an outer-core cladding 515 with refractive index ($n_{clad1}$) and the inner core fibers 505 can be contained within an inner-core cladding 520 with refractive index ($n_{clad2}$). Also, the outer core 510 has a core diameter ($d_{core2}$) and the inner cores 505 can have a core diameter ($d_{core1}$).

Figure 5B:
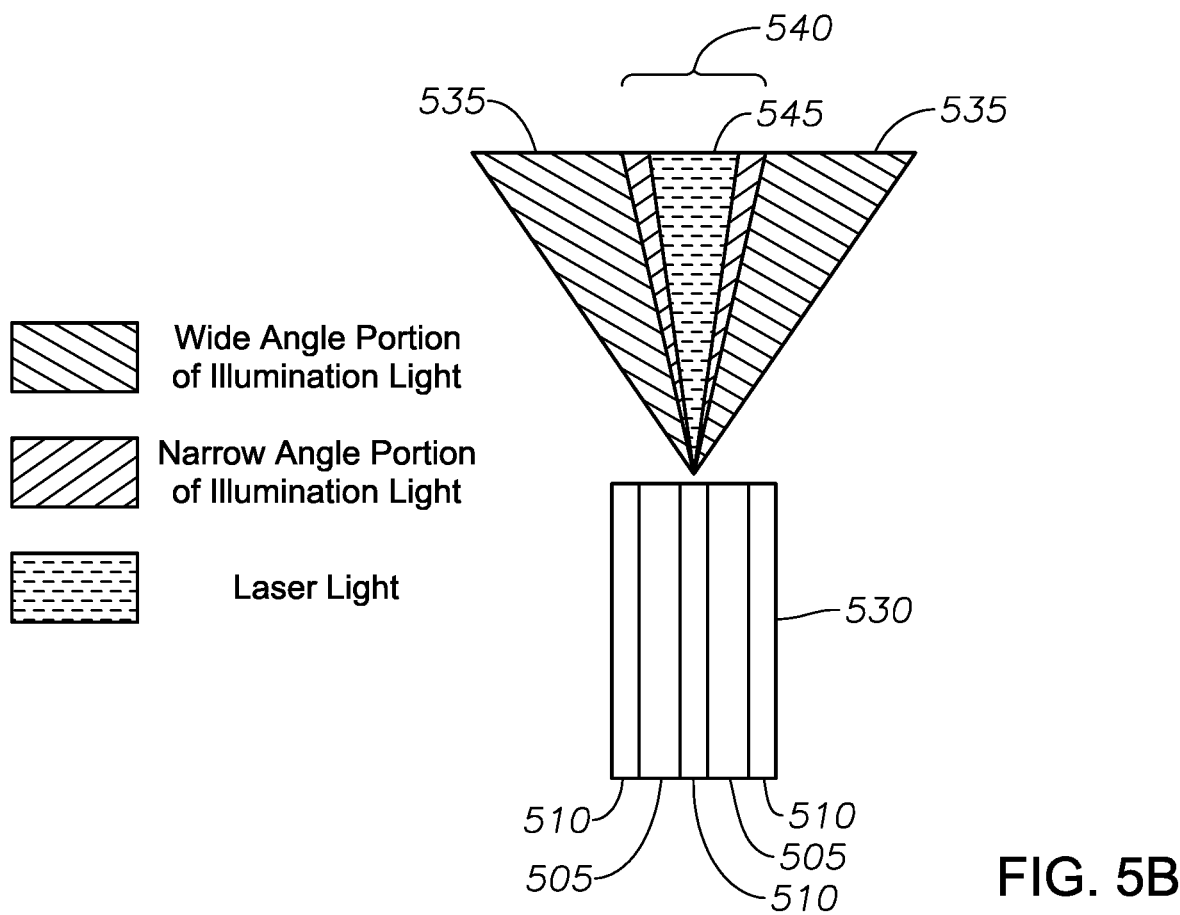
FIG. 5B illustrates a side view of the interface of a plurality of light cones onto a multi-core optical fiber cable in accordance with a particular embodiment of the present disclosure.

FIG. 5B illustrates a side view of the interface of a plurality of light cones 535, 540, 545 onto a terminal end of a multi-core optical fiber cable 530 according to some embodiments of the present disclosure. The multi-core optical fiber cable 530 in FIG. 5B shows the outer core fiber 510 and two of the inner core fibers 505. For the sake of image clarity, the outer-core cladding 515 and the inner-core cladding 520 is not depicted in FIG. 5B. Also represented are a wide-angle portion of the illumination light cone 535, a narrow-angle portion of the illumination light cone 540, and the laser light cone 545. The selection of the condensing lens is related to the half-angle of each of the light cones. Therefore, selecting a condensing lens can involve selecting a condensing lens based on the NA of the light, the acceptance angle of the light cones, and the refractive indices of the materials of the outer core fiber 510, the outer-core cladding 515, the inner core fibers 505, and the inner-core cladding 520.

The condensing lens is designed to focus laser light down onto the multi-core fiber interface with the desired beam NA. The refractive indices of the inner core fibers 505 and inner cladding-core claddings 520 are selected according to an NA calculation (shown below) so that the NA of the inner cores is equal to or greater than the beam NA, thereby ensuring confinement of the beams within the inner core regions as they propagate down the lengths of the inner core fibers 505.

Referring again to FIG. 5A, a refractive index ($n_{core2}$) of the outer core fiber 510 is greater than a refractive index ($n_{clad2}$) of the outer-core cladding 515. Also, a refractive index ($n_{core1}$) of each of the inner cores fibers 505 is greater than a refractive index ($n_{clad1}$) of the inner-core cladding 520. Further, the refractive index ($n_{core1}$) of each or the inner cores fibers 505 is larger than the refractive index ($n_{clad1}$) of the outer-core cladding 515.

The numerical aperture (NA$_2$) for the outer core fiber 510 and the outer-core cladding 515 can be calculated as:

$$NA_2 = \sqrt{(n_{core2})^2 - (n_{clad2})^2}$$

Likewise, the numerical aperture (NA$_1$) for the inner core fibers 505 and the inner-core cladding 520 can be calculated as:

$$NA_1 = \sqrt{(n_{core1})^2 - (n_{clad1})^2}$$

In some embodiments of the present disclosure, the materials for the outer core fiber 510, the outer-core cladding 515, the inner core fibers 505, and the inner-core cladding 520 are selected such that NA$_2$ is much larger than NA$_1$. In a specific embodiment, the outer core can be an undoped fused silica with an index of substantially 1.46.

Also, in some embodiments, the red aiming laser beam has an NA of about 0.044 and the green treatment laser beam has an NA of about 0.0657. Therefore, as long as the numerical aperture (NA$_1$) for the inner core fiber 505 is larger than 0.0657, the red and green laser beams will remain confined within the inner cores 505 as they propagate down the probe. So, a silica fiber with an NA of 0.22 used for the outer core 510 may confine the laser beams.

Also, the illumination light can have an NA of around 0.63 and the core diameter can be configured to under-fill or match d$_{core2}$. The numerical aperture (NA$_2$) for the outer core fiber 510 and the outer-core cladding 515 can be designed to have a fiber NA≥0.63, e.g. a borosilicate fiber construction.

When the illumination beam etendue is greater than outer core 510 etendue, then coupling efficiency into outer core 510 is less than one hundred percent regardless of condenser lens focal length choice. However, if the illumination beam etendue (which is the product of the illumination beam angular width and spot width) is less than the outer core 510 etendue, then one hundred percent coupling efficiency (neglecting Fresnel reflection losses) can occur if the condensing lens focus is designed correctly. If the condensing lens has too short of a focus, the converging beam may have an NA greater than core 510 NA, and coupling efficiency may be degraded. If the condensing lens has too long of a focal length, then the focused beam diameter may be larger than the 510 diameter, and coupling efficiency may be degraded. However if the condensing lens focal length is adjusted so that beam NA is less than or equal to the fiber NA, and the beam diameter is less than or equal to the fiber core diameter, then one hundred percent or near one hundred percent coupling efficiency can occur.

Therefore, the illumination beam may both spatially and angularly underfill the outer core 510, which will permit spatial and angular misalignments without a loss of coupling efficiency. Also, since the illumination beam NA is» NA$_1$, off-axis rays can frequently pass in and out of the inner cores 505 and inner core cladding 520 as the rays propagate down the length of the multi-core optical fiber cable 530.

Figure 5C:
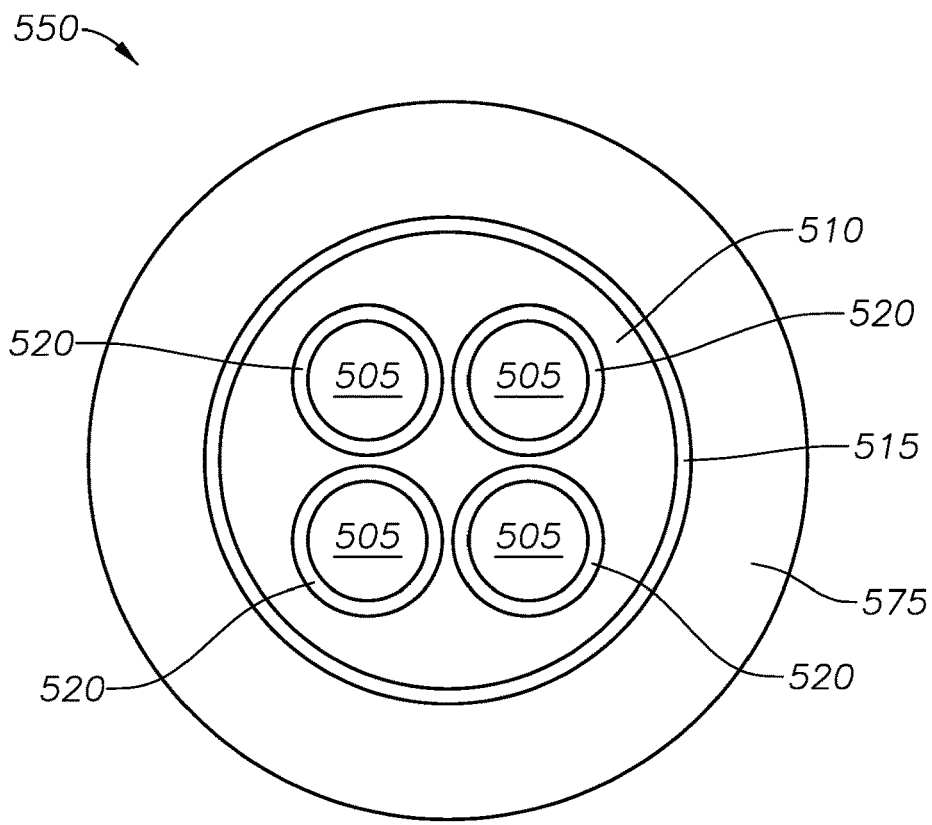
FIG. 5C illustrates the cut-away view of a multi-core optical fiber cable according to some embodiments of the present technology in accordance with a particular embodiment of the present disclosure.

FIG. 5C illustrates the cut-away view of a multi-core optical fiber cable 550 according to some embodiments of the present disclosure. The multi-core fiber cable 550 includes four fused silica inner core fibers 505 with a 75 micrometer diameter and a numerical aperture (NA) of 0.22 inside of a non-doped fused silica outer core fiber 510 having a 300 micrometer diameter and an NA of 0.47. The outer core fiber 510 can be contained within low-index polymer cladding 515 having a 25 micrometer thickness and the inner core fibers 505 can be contained within fluorine-doped fused silica inner-core cladding 520 having a 15 micrometer thickness. The multi-core optical fiber cable 550 can be further contained in an Ethylene Tetrafluoroethylene (ETFE) coating 575.

The four fused silica inner core fibers 505 have a refractive index of 1.46 at 532 nanometers. The non-doped fused silica outer core fiber 510 have a refractive index of 1.46 at 532 nanometers. The fluorine-doped fused silica inner-core cladding 520 can have a refractive index of 1.4433 at 532 nanometers. The low-index polymer cladding 515 can have a refractive index of 1.38228 at 532 nanometers.

Figure 5D:
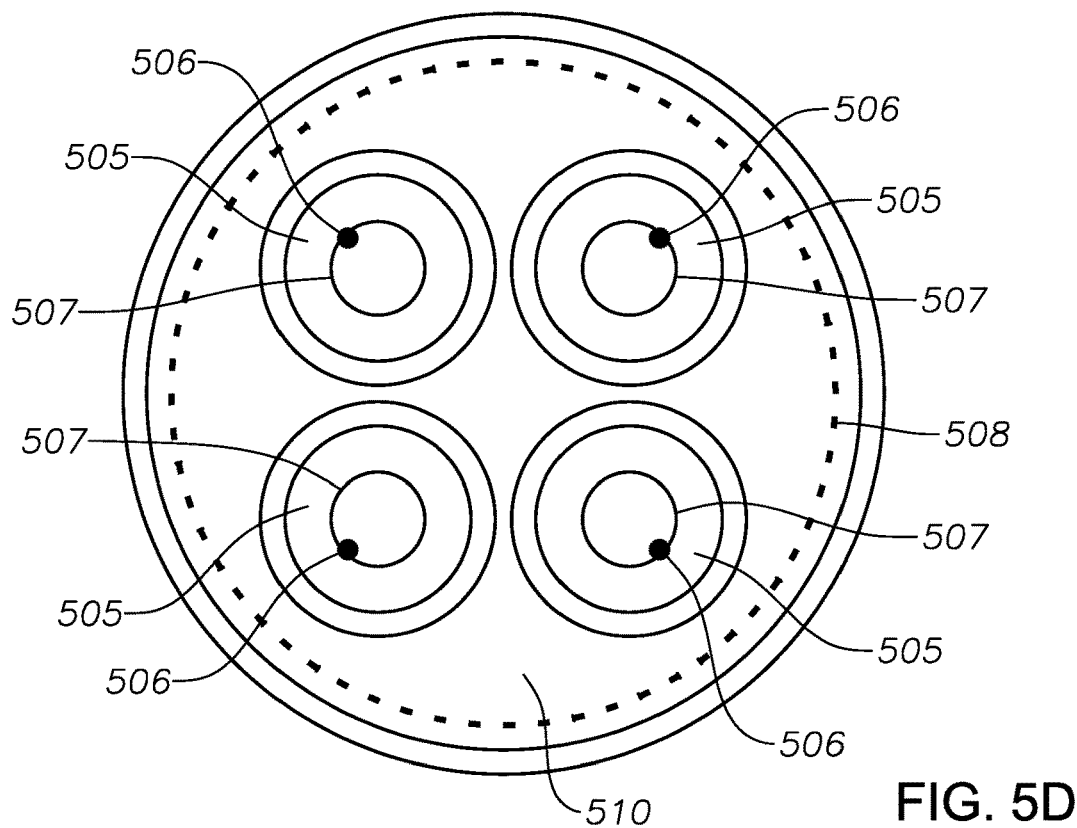
FIG. 5D illustrates a proximal, interface end of a multi-core optical fiber cable with laser beam spots lining up with the inner cores and an illumination light beam spot lining up with the outer core in accordance with a particular embodiment of the present disclosure.
Figure 5E:
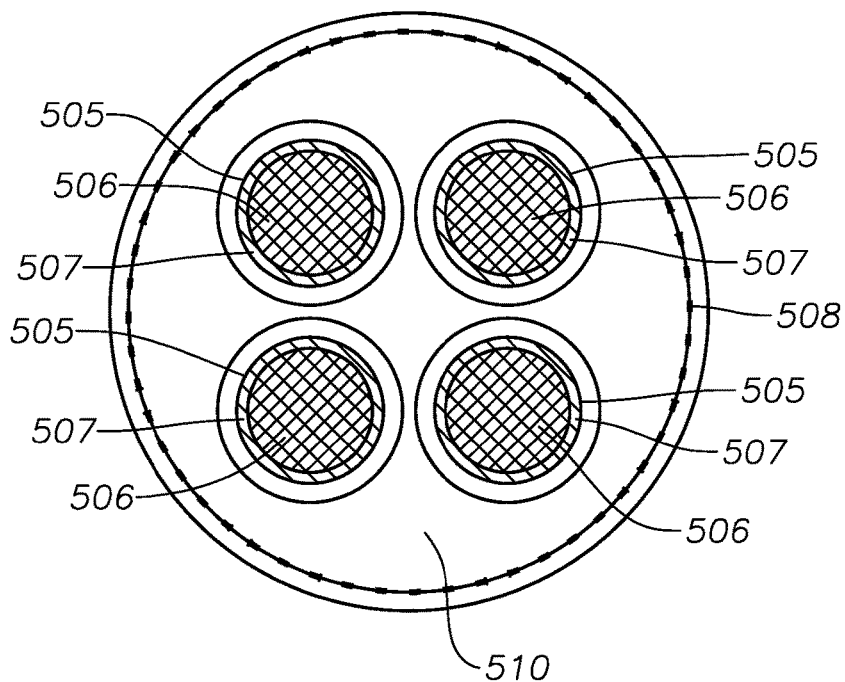
FIG. 5E illustrates the distal end of a multi-core optical fiber cable with all three beams spread out to totally spatially fill their respective cores in accordance with a particular embodiment of the present disclosure.

FIG. 5D illustrates a proximal, interface end of the multi-core optical fiber cable with a red laser aiming beam spot 506 and a green laser treatment beam spot 507 lining up with the inner cores 505 and the illumination light beam spot 508 lining up with the outer core 510. FIG. 5E illustrates the distal end of the multi-core optical fiber cable with all three beams spread out to totally spatially fill their respective cores. FIGS. 5F-5L illustrate the propagation of the multiplexed light through the multi-core optical fiber cable.

Figure 5F:
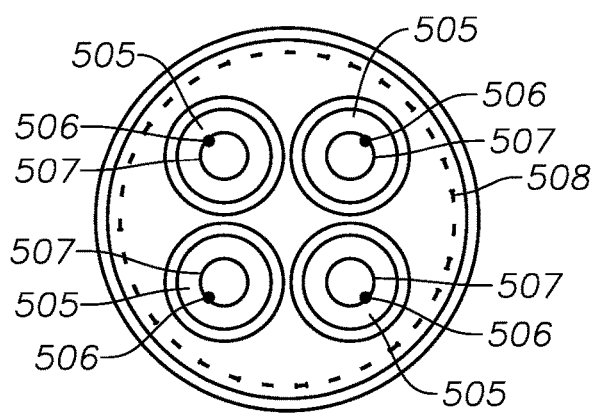
Figure 5G:
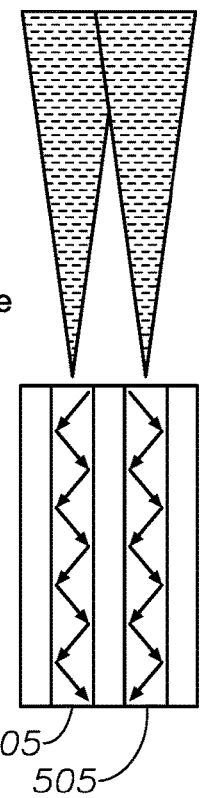
Figure 5H:
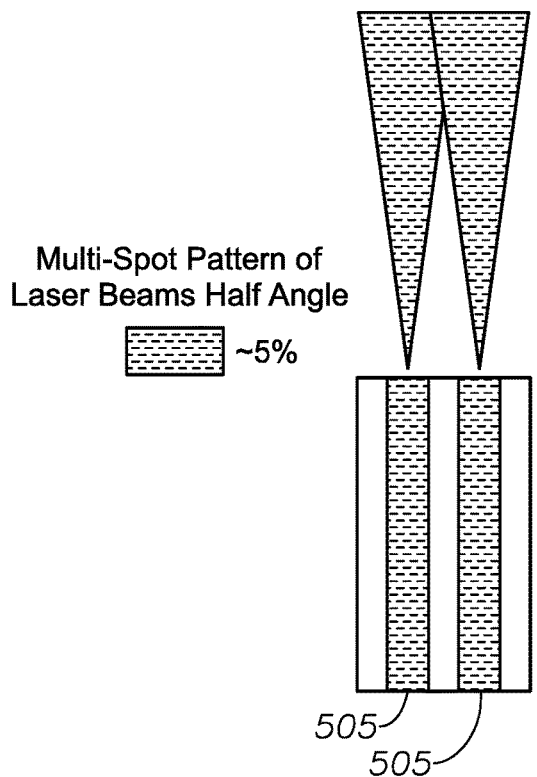
Figure 5I:
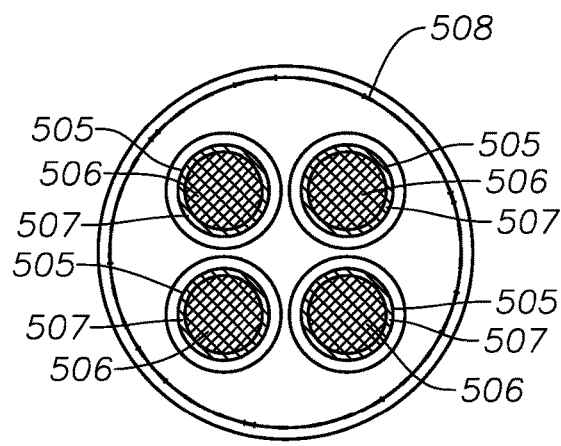

FIG. 5F illustrates a proximal, interface end of the multi-core optical fiber cable with a red laser aiming beam spot 506 and a green laser treatment beam spot 507 lining up with the inner cores 505. FIG. 5G illustrates two light cones from the multi-spot pattern of laser light (with the multiplexed illumination light emitted for image clarity) propagating down the lengths of a multi-core optical fiber cable. FIG. 5H illustrates the laser beams spread out to totally spatially fill the inner cores 505. Similarly, FIG. 5I illustrates the distal end of the multi-core optical fiber cable with the laser beams spread out to totally spatially fill the inner cores 505.

Figure 5J:
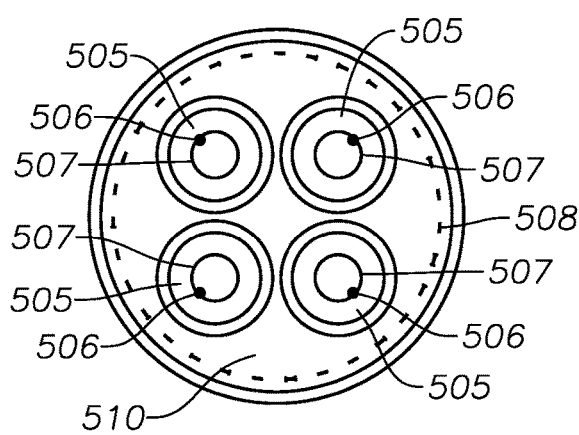
Figure 5K:
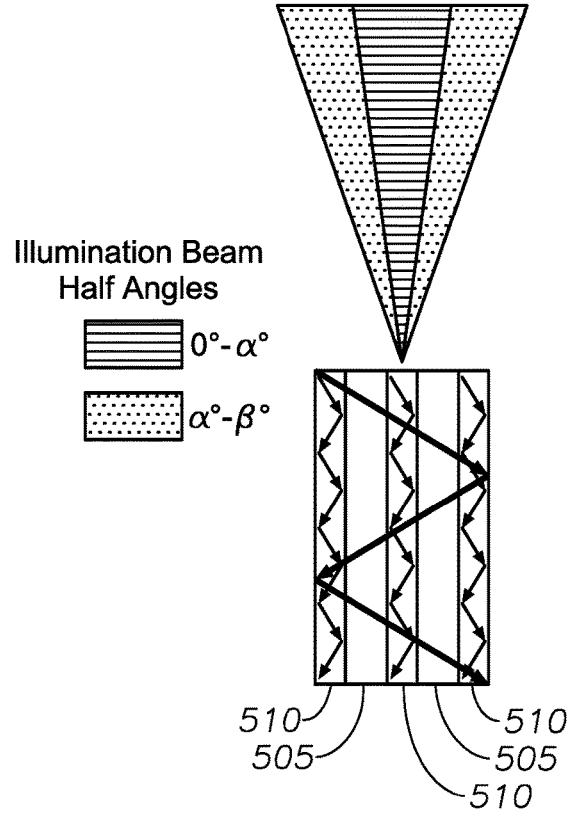

FIG. 5J illustrates a proximal, interface end of the multi-core optical fiber cable with the illumination light spot lining up with the outer core 510. FIG. 5K illustrates a light cone of the illumination light (with the multiplexed multi-spot pattern of laser light beams emitted for image clarity), with the light cone including a narrow half-angle portion of the light cone and a wide half-angle portion. The narrow half-angle portion of the light cone propagates the lengths of the outer cores 510, but is excluded from the inner cores 505. The wide half-angle portion of the illumination light cone fills the length of the outer core 510 and the inner cores 505.

FIG. 5L illustrates the illumination beam spread out to totally spatially fill the outer core 510. Similarly, FIG. 5M illustrates the distal end of the multi-core optical fiber cable with the illumination beam spread across the outer cores 510 and the inner cores 505.

FIG. 5N illustrates the cut-away view of another multi-core optical fiber cable 580 according to some embodiments of the present technology. The multi-core fiber cable 580 includes four germanium-doped silica inner core fibers 585 with a 75 micrometer diameter and a numerical aperture (NA) of 0.22 inside of a non-doped fused silica outer core fiber 590 having a 300 micrometer diameter and an NA of 0.47. The outer core fiber 590 can be contained within low-index polymer cladding 595 having a 25 micrometer thickness. The multi-core optical fiber cable 580 can be further contained in an Ethylene Tetrafluoroethylene (ETFE) coating 576.

The four germanium-doped silica inner core fibers 585 have a refractive index of substantially 1.47648 at 532 nanometers. The non-doped fused silica outer core fiber 590 have a refractive index of 1.46 at 532 nanometers. The low-index polymer cladding 595 can have a refractive index of 1.38228 at 532 nanometers.

While specific geometries of the multi-core optical fiber cable are shown explicitly herein, those with ordinary skill in the art having the benefit of the present disclosure will readily appreciate that a wide variety of configurations for the multi-core optical fiber cable are possible. In the configuration shown in FIGS. 5A-5N, the white illumination spot at the distal end of the multi-core optical fiber is somewhat larger than the 2×2 array of laser spots. In some cases, this geometry is desired, because it provides illumination into both the retinal treatment target area as well as some surrounding retina and because the illumination spot small enough to keep the white light fairly concentrated. Also, the geometry enables adequate white irradiance at the retina with a relatively small core diameter fiber. Furthermore, as explained above, the intensities of the white illumination and the laser aiming beams can be adjusted (e.g., at the Illumination Light Source and Surgical Laser System, respectively) to provide the right amount of laser aiming beam contrast against the white while providing enough white illumination to easily see the retina.

In some embodiments of the present technology, the distal end of the multi-core optical fiber cable terminates within a tip of a surgical hand probe that is inserted into a patient's eye. The tip of the surgical hand probe can also include a lens to image the multiplexed beams onto patient anatomy, e.g. the retina.

FIG. 6A illustrates an open side view of a tip 605 of a surgical hand probe according to some embodiments of the present disclosure. The probe tip 605 can comprise a cannula 635 (e.g. a stainless steel cannula) with a cannula distal end 630 and the probe tip containing the multi-core optical fiber 610 and a lens 615. The lens 615 can be a graded-index (GRIN) lens and an air gap 625 can be left open between the GRIN lens 615 and the distal end of the multi-core optical fiber 610. The air gap 625 can be sized such that the light emitted from the multi-core optical fiber 610 experiences an amount of spread before falling incident on the GRIN lens 615 and such that the GRIN lens 615 images the light onto the patient anatomy.

In some cases, no air gap is allowed between the distal end of the multi-core optical fiber 610 and the proximal end of the lens 615. Here, the multi-core optical fiber 610 and lens 615 are substantially butted up against one other with positive pressure to avoid air-gap tolerance concerns, allowing less chance for peripheral off-axis rays to travel far enough off axis to reflect off of the cylindrical side wall of the GRIN lens. However, using a conventional lens instead of the GRIN lens involves an air gap between the multi-core optical fiber 610 and lens 615 to focus the light properly.

In some cases, the lens 615 is secured within the probe tip 605 with an optical adhesive 620. As shown in FIG. 6A, a multi-spot pattern of green, 532 nm laser light is projected retinal tissue located 4 millimeters from the cannula distal end 630.

FIG. 6B illustrates an open side view of another tip 640 of a surgical hand probe according to some embodiments of the present disclosure. Again, the probe tip 640 can comprise a cannula 645 with a cannula distal end 650 and the probe tip containing the multi-core optical fiber 655 and a lens 660. The lens 660 illustrated in FIG. 6B is a Plano-convex glass lens. Also, the Plano-convex lens 660 is secured in the cannula 635 by a retaining feature 665. Again, an air gap 670 can be sized such that the light emitted from the multi-core optical fiber 655 experiences an amount of spread before falling incident on the Plano-convex lens 660 and such that the Plano-convex lens 660 images the light onto the patient anatomy.

Figure 7:
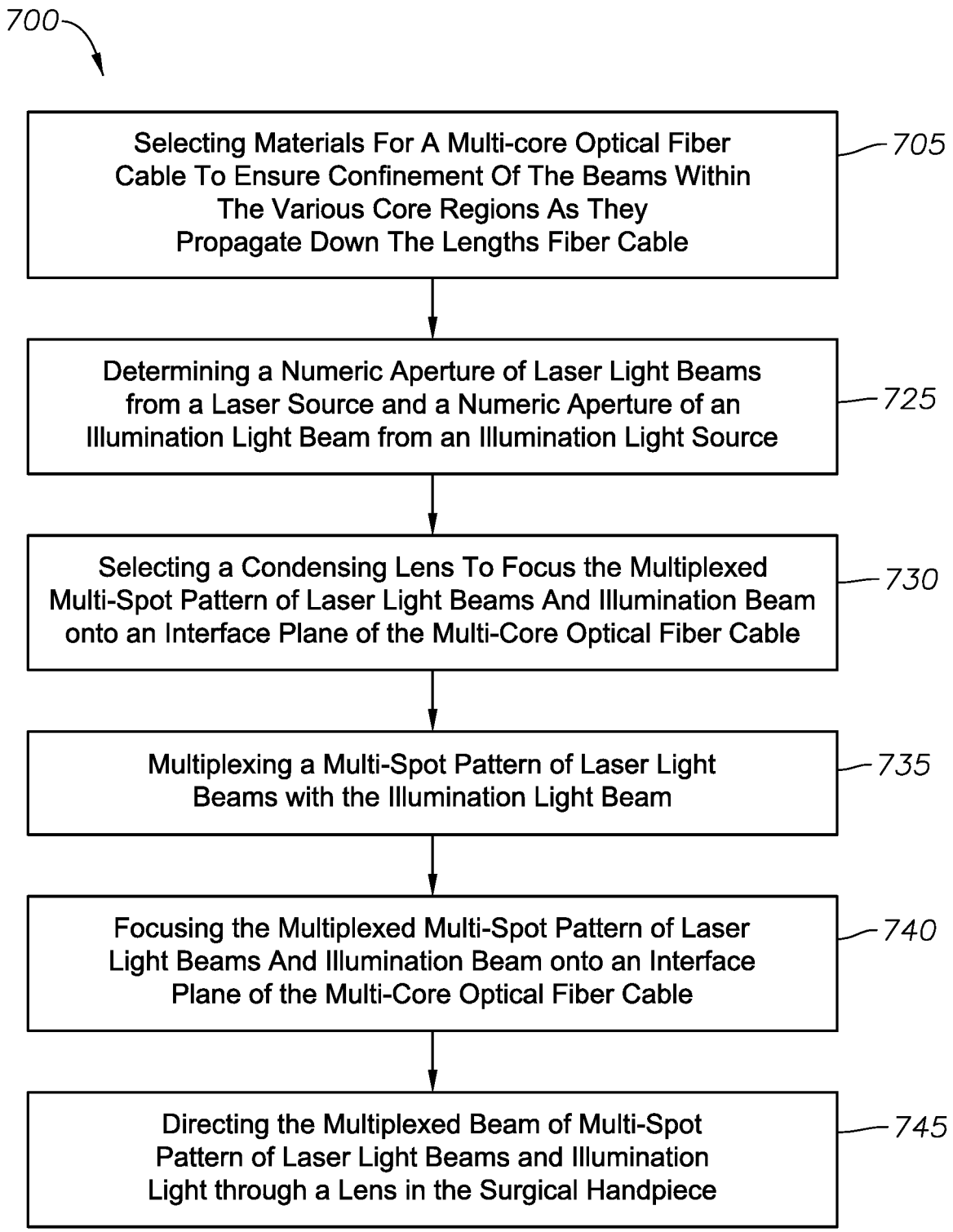
FIG. 7 illustrates a method of creating an image of a multiplexed beam of multi-spot pattern of laser light beams and illumination light in accordance with a particular embodiment of the present disclosure.

FIG. 7 illustrates a method 700 of creating an image of a multiplexed beam of multi-spot pattern of laser light beams and illumination light in accordance with a particular embodiment of the present disclosure. The method involves: selecting materials for a multi-core optical fiber cable to ensure confinement of the beams within the various core regions as they propagate down the lengths fiber cable at step 705, as explained above. The method 700 also involves determining a numerical aperture of laser light beams from a laser source and a numerical aperture of an illumination light beam from an illumination light source at step 725 and selecting a condensing lens to focus the multiplexed multi-spot pattern of laser light beams and illumination beam onto an interface plane of the multi-core optical fiber cable at step 730.

Next, the method 700 involves multiplexing a multi-spot pattern of laser light beams with the illumination light beam at step 735, focusing the multiplexed multi-spot pattern of laser light beams and illumination beam onto an interface plane of the multi-core optical fiber cable at step 740, and directing the multiplexed beam of multi-spot pattern of laser light beams and illumination light through a lens in the surgical handpiece at step 745.

As explained above, a wide variety of configurations for the multi-core optical fiber cable are possible. For example, an incoherent white light illumination light source can be replaced with a white laser system (e.g., a supercontinuum laser system). In this case, the etendue of the white laser beam is small enough that it is less than the nanofiber etendue and can be efficiently coupled into the nanofiber, such that a multi-core optical fiber cable as described above can be used to deliver multiplexed laser aiming and treatment beams and white laser illumination.

Figure 8A:
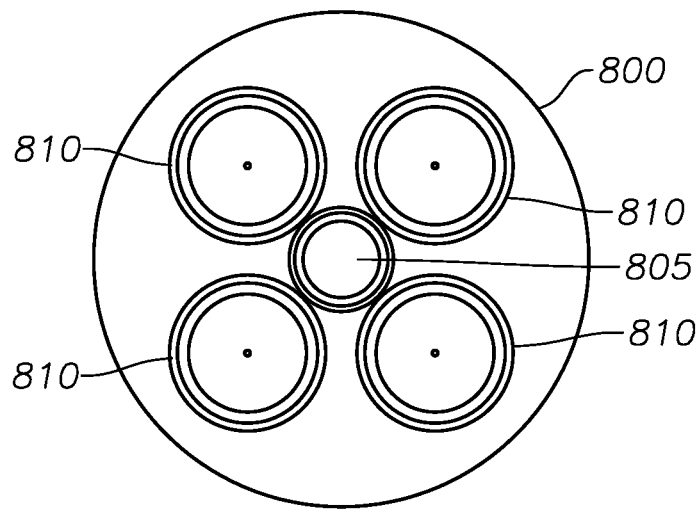
FIG. 8A illustrates an end view of a multi-lumen tubing for delivering multiplexed laser aiming and treatment beams and a laser illumination light beam in accordance with a particular embodiment of the present disclosure.

FIGS. 8A-8D illustrate another example of a system for multiplexing laser aiming and treatment beams and illumination light. FIG. 8A illustrates an end view of a multi-lumen tubing 800 for delivering multiplexed laser aiming and treatment beams and a laser illumination light beam. The multi-lumen tubing 800 includes a central nanofiber 805 and an array of glass laser fibers 810 contained within the multi-lumen tubing 800. The central nanofiber 805 can be a large NA fiber for carrying a white laser beam and the glass laser fibers 810 can be small diameter, small NA glass fibers for carrying laser aiming and treatment beams (e.g. red aiming beams and green treatment beams). In some cases, the central nanofiber 805 can be enclosed within a tiny-diameter, rigid, cylindrical or square, black absorptive or reflective cannula for structural support, and can optionally be attached a focusing lens (described below) for structural support as well.

Figure 8B:
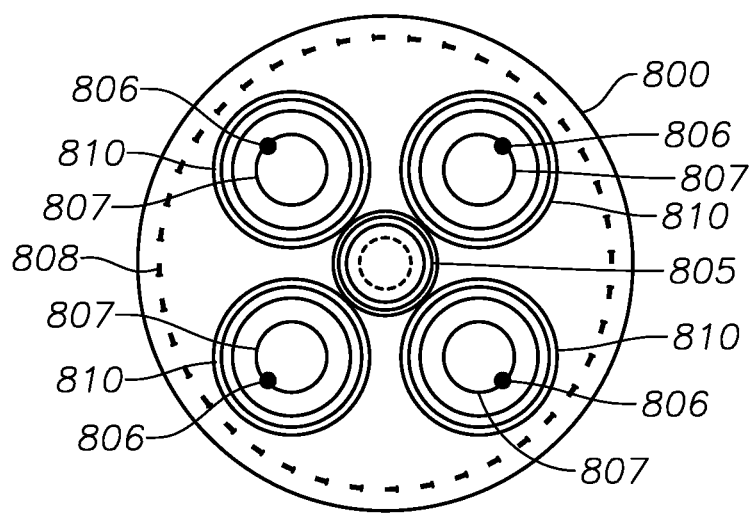
FIG. 8B illustrates each of the laser aiming and treatment beams as well as the laser illumination light beam spatially underfilling their respective fiber cores at the proximal end in accordance with a particular embodiment of the present disclosure.
Figure 8C:
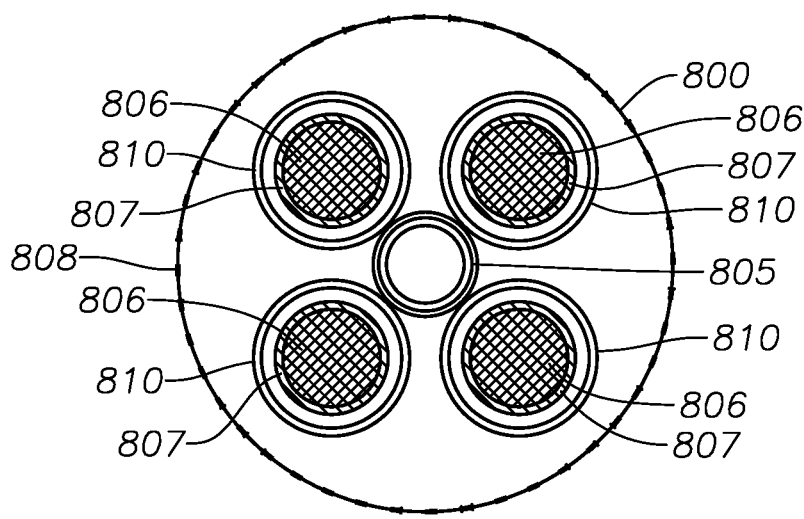
FIG. 8C illustrates each of the laser aiming and treatment beams as well as the laser illumination light beam spatially totally filling their cores at the distal end in accordance with a particular embodiment of the present disclosure.
Figure 8D:
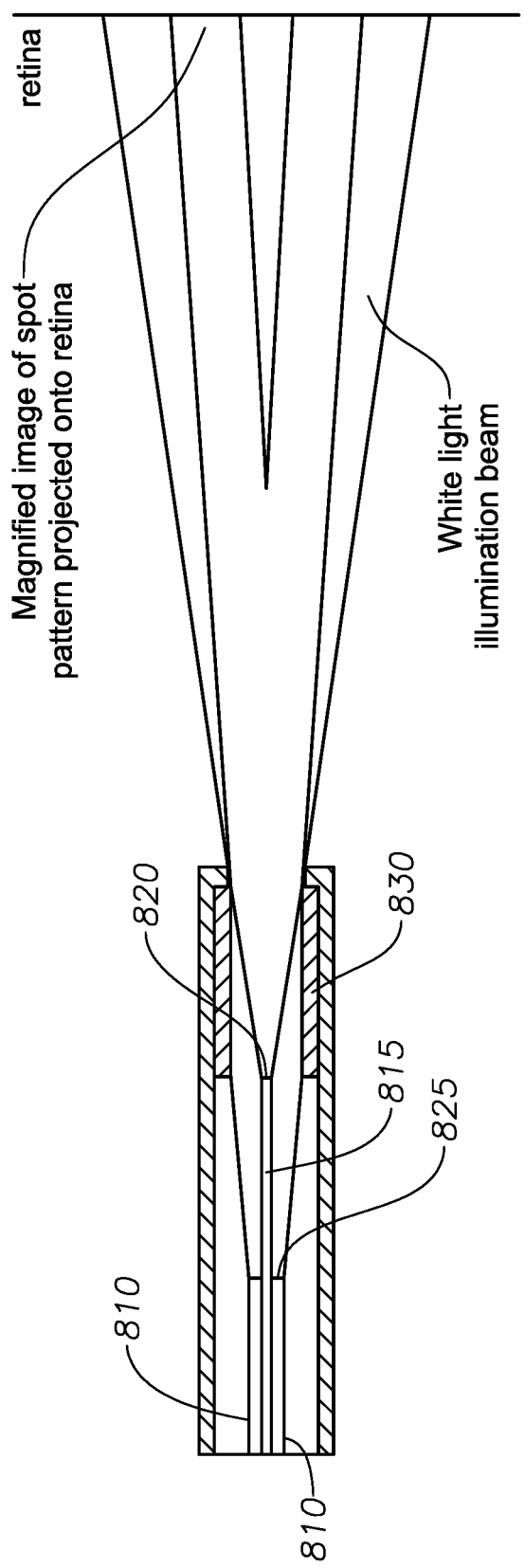
FIG. 8D illustrates a distal end of a nanofiber extending past an array of glass fibers in the multi-lumen tubing at or near a focusing lens in accordance with a particular embodiment of the present disclosure.

As shown in FIGS. 8B-8C, each of the laser aiming beams 806 and laser treatment beams 807 as well as the laser illumination light beam 808 will spatially underfill their respective fiber cores at the proximal end (FIG. 8B), but will totally fill their cores at the distal end (FIG. 8C). In this case, in order to have the white laser illumination beam spatially larger than the multi-spot laser beam pattern at the retina, it is necessary to extend the distal end 820 of the nanofiber 815 past the distal end 825 of the array of glass fibers 810 in the multi-lumen tubing 800 until the distal end 820 of the nanofiber 815 is at or near a proximal end of a focusing lens 830 (e.g., a plano-convex lens), as shown in FIG. 8D.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An illumination and multi-spot laser multiplexing system comprising:
    a laser source that emits a collimated laser light beam;
    a diffractive optical element (DOE) configured to receive the collimated laser light beam and to create a multi-spot pattern of laser light beams; and
    an illumination system that emits an illumination light;
    a collimating lens that collimates the illumination light received from the illumination system;
    a multi-core optical fiber cable;
    a fiber optic cable port configured to couple with the multi-core optical fiber cable;
    a condensing lens; and
    a beamsplitter configured to reflect the multi-spot pattern of laser light beams towards the condensing lens and to transmit an illumination beam from the collimating lens towards the condensing lens, thereby multiplexing the multi-spot pattern of laser light beams and the illumination beam,
    wherein the condensing lens is configured to focus the multiplexed multi-spot pattern of laser light beams and the illumination beam onto an interface with the fiber optic cable port;
    wherein the condensing lens is configured to focus the multiplexed multi-spot pattern of laser light beams and the illumination beam onto an interface of a proximal end of the multi-core optical fiber cable such that the illumination beam is propagated down an entire length of an outer core of the multi-core optical fiber cable and such that each laser light beam in the multi-spot pattern of laser light beams propagates down an entire length of one of a plurality of inner cores contained within the outer core.

2. The illumination and multi-spot laser multiplexing system of claim 1, wherein the DOE is housed within a linear slide configured to alternatively position the DOE in a beam path of the collimated laser light beam.

3. The illumination and multi-spot laser multiplexing system of claim 1, wherein the laser source, the DOE, the illumination system, the collimating lens, the fiber optic cable port, the beamsplitter, and the condensing lens are integrated within a surgical console configured to perform one or more ophthalmic procedures.

4. The illumination and multi-spot laser multiplexing system of claim 1, wherein the beamsplitter reflects light in a first narrow band and in a second narrow band, and wherein the beamsplitter transmits the illumination light outside of the first narrow band and the second narrow band.

5. The illumination and multi-spot laser multiplexing system of claim 4, wherein the laser source comprises a user-selectable laser source configured to alternatively emit laser light beams having a wavelength contained within at least one of two narrow bands of an electromagnetic spectrum of light that correspond to a surgical treatment beam having a wavelength of 532 nm and to a surgical aiming beam having a wavelength of 635 nm.

6. An illumination and multi-spot laser multiplexing system comprising:
    a laser source that emits a collimated laser light beam;
    an illumination system that emits an illumination light;
    a collimating lens that collimates the illumination light received from the illumination system;

a condensing lens;

a beamsplitter configured to reflect the collimated laser light beam towards the condensing lens and to transmit a collimated illumination beam from the collimating lens towards the condensing lens, thereby multiplexing the collimated laser light beam and the collimated illumination beam;

a diffractive optical element (DOE) configured to receive the multiplexed laser light beam and illumination beam and to create a multi-spot pattern of laser light beams within the illumination beam;

a multi-core optical fiber cable; and a fiber optic cable port configured to couple with the multi-core optical fiber cable;

wherein the condensing lens is configured to focus the multiplexed multi-spot pattern of laser light beams and the illumination beam onto an interface with the fiber optic cable port;

wherein the condensing lens is configured to focus the multiplexed multi-spot pattern of laser light beams and the illumination beam onto an interface of a terminal end of the multi-core optical fiber cable such that the illumination beam is propagated down an entire length of an outer core of the multi-core optical fiber cable and such that each laser light beam in the multi-spot pattern of laser light beams propagates down an entire length of one of a plurality of inner cores contained within the outer core.

7. The illumination and multi-spot laser multiplexing system of claim 6, wherein the DOE is housed within a linear slide configured to alternatively position the DOE in a beam path of the collimated laser light beam.

8. The illumination and multi-spot laser multiplexing system of claim 6, wherein the laser source, the DOE, the illumination system, the collimating lens, the fiber optic cable port, the beamsplitter, and the condensing lens are integrated within a surgical console configured to perform one or more ophthalmic procedures.

9. The illumination and multi-spot laser multiplexing system of claim 6, wherein the beamsplitter reflects light in a first narrow band and in a second narrow band, and wherein the beamsplitter transmits the illumination light outside of the first narrow band and the second narrow band.

10. The illumination and multi-spot laser multiplexing system of claim 9, wherein the laser source comprises a user-selectable laser source configured to alternatively emit laser light beams having a wavelength contained within at least one of two narrow bands of an electromagnetic spectrum of light that correspond to a surgical treatment beam having a wavelength of 532 nm and to a surgical aiming beam having a wavelength of 635 nm.

* * * * *